US007105103B2

(12) United States Patent
Keenan et al.

(10) Patent No.: US 7,105,103 B2
(45) Date of Patent: Sep. 12, 2006

(54) SYSTEM AND METHOD FOR THE MANUFACTURE OF SURGICAL BLADES

(75) Inventors: Joseph Francis Keenan, Cohasset, MA (US); Vadim Mark Daskal, Watertown, MA (US); James Joseph Hughes, Dracut, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 441 days.

(21) Appl. No.: 10/383,573

(22) Filed: Mar. 10, 2003

(65) Prior Publication Data

US 2003/0199165 A1    Oct. 23, 2003

Related U.S. Application Data

(60) Provisional application No. 60/430,332, filed on Dec. 3, 2002, provisional application No. 60/362,999, filed on Mar. 11, 2002.

(51) Int. Cl.
| | |
|---|---|
| *B24C 1/22* | (2006.01) |
| *C03C 15/00* | (2006.01) |
| *C03C 25/68* | (2006.01) |
| *C23F 1/00* | (2006.01) |
| *C23F 3/00* | (2006.01) |

(52) U.S. Cl. ............... 216/101; 438/745; 438/753; 252/79.2

(58) Field of Classification Search ............... 438/714, 438/719, 745, 753
See application file for complete search history.

(56) References Cited

U.S. PATENT DOCUMENTS

| 3,543,402 A | 12/1970 | Seager |
|---|---|---|
| 3,803,963 A | 4/1974 | Hunt |
| 3,831,466 A | 8/1974 | Hicks, Jr. |
| 3,834,265 A | 9/1974 | Tafapolsky |
| 3,857,488 A | 12/1974 | Cren |
| 3,894,337 A | 7/1975 | Jones |
| 3,942,231 A | 3/1976 | Whitaker |
| 4,091,813 A | 5/1978 | Shaw |

(Continued)

FOREIGN PATENT DOCUMENTS

DE    3526951    1/1987

(Continued)

OTHER PUBLICATIONS

Wolf et al., Silicon Processing for the VLSI Era, 1986, vol. 1, p. 531.*

(Continued)

*Primary Examiner*—Duy-Vu N. Deo
(74) *Attorney, Agent, or Firm*—Roylance, Abrams, Berdo & Goodman LLP; James J. Murtha

(57) ABSTRACT

A method for manufacturing surgical blades from either a crystalline or poly-crystalline material, preferably in the form of a wafer, is disclosed. The method includes preparing the crystalline or poly-crystalline wafers by mounting them and machining trenches into the wafers. The methods for machining the trenches, which form the bevel blade surfaces, include a diamond blade saw, laser system, ultrasonic machine, and a hot forge press. The wafers are then placed in an etchant solution which isotropically etches the wafers in a uniform manner, such that layers of crystalline or poly-crystalline material are removed uniformly, producing single or double bevel blades. Nearly any angle can be machined into the wafer which remains after etching. The resulting radii of the blade edges is 5–500 nm, which is the same caliber as a diamond edged blade, but manufactured at a fraction of the cost.

49 Claims, 24 Drawing Sheets

U.S. PATENT DOCUMENTS

| | | | |
|---|---|---|---|
| 4,122,602 A | 10/1978 | Sastri |
| 4,219,025 A | 8/1980 | Johnson |
| 4,231,371 A | 11/1980 | Lipp |
| 4,232,676 A | 11/1980 | Herczog |
| 4,248,231 A | 2/1981 | Herczog |
| 4,318,537 A | 3/1982 | Dorman |
| 4,409,659 A | 10/1983 | Devine |
| 4,413,970 A | 11/1983 | Seng |
| 4,444,102 A | 4/1984 | Clark |
| 4,468,282 A | 8/1984 | Neukermans |
| 4,509,651 A | 4/1985 | Prindle |
| 4,534,827 A | 8/1985 | Henderson |
| 4,551,192 A | 11/1985 | Di Milia |
| 4,566,465 A | 1/1986 | Arhan et al. |
| 4,579,022 A | 4/1986 | Kasai |
| 4,581,969 A | 4/1986 | Kim |
| 4,587,202 A | 5/1986 | Borysko |
| 4,611,400 A | 9/1986 | Drake |
| 4,629,373 A | 12/1986 | Hall |
| 4,634,496 A | 1/1987 | Mase et al. |
| 4,671,849 A | 6/1987 | Chen |
| 4,686,980 A | 8/1987 | Williams et al. |
| 4,688,570 A | 8/1987 | Kramer |
| 4,697,489 A | 10/1987 | Kim |
| 4,719,915 A | 1/1988 | Porat et al. |
| 4,735,202 A | 4/1988 | Williams |
| 4,735,920 A | 4/1988 | Stephani et al. |
| 4,740,410 A | 4/1988 | Muller |
| 4,777,096 A | 10/1988 | Borysko |
| 4,790,812 A | 12/1988 | Hawkins, Jr. et al. |
| 4,793,218 A | 12/1988 | Jordan et al. |
| 4,798,000 A | 1/1989 | Bedner et al. |
| 4,808,260 A | 2/1989 | Sickafus |
| 4,846,250 A | 7/1989 | Bedner et al. |
| 4,850,353 A | 7/1989 | Stasz et al. |
| 4,862,890 A | 9/1989 | Stasz et al. |
| 4,872,947 A | 10/1989 | Wang et al. |
| 4,911,782 A | 3/1990 | Brown |
| 4,916,002 A | 4/1990 | Carver |
| 4,922,903 A | 5/1990 | Welch et al. |
| 4,934,103 A | 6/1990 | Campergue |
| 4,948,461 A | 8/1990 | Chatterjee |
| 4,955,894 A | 9/1990 | Herman |
| 4,958,539 A | 9/1990 | Stasz et al. |
| 4,980,021 A | 12/1990 | Kitamura |
| 5,019,035 A | 5/1991 | Missirlian et al. |
| 5,021,364 A | 6/1991 | Akamine et al. |
| 5,032,243 A | 7/1991 | Bache |
| 5,048,191 A | 9/1991 | Hahn |
| 5,056,277 A | 10/1991 | Wilson |
| 5,077,901 A | 1/1992 | Warner et al. |
| 5,082,254 A | 1/1992 | Hunnell |
| 5,100,506 A | 3/1992 | Sturtevant |
| 5,121,660 A | 6/1992 | Kramer |
| 5,142,785 A | 9/1992 | Grewal et al. |
| 5,143,785 A | 9/1992 | Grewal et al. |
| 5,166,520 A | 11/1992 | Prater |
| 5,176,628 A | 1/1993 | Charles et al. |
| 5,193,311 A | 3/1993 | Dawson |
| 5,201,992 A | 4/1993 | Marcus |
| 5,217,477 A | 6/1993 | Lager |
| 5,222,967 A | 6/1993 | Casebeer et al. |
| 5,258,002 A | 11/1993 | Jeffers |
| 5,266,528 A | 11/1993 | Yamada |
| 5,295,305 A | 3/1994 | Hahn et al. |
| 5,317,938 A | 6/1994 | de Juan, Jr. |
| 5,342,370 A | 8/1994 | Simon et al. |
| 5,474,532 A | 12/1995 | Steppe |
| 5,562,693 A | 10/1996 | Devlin et al. |
| 5,579,583 A | 12/1996 | Mehregany |
| 5,609,778 A | 3/1997 | Pulaski et al. |
| 5,619,889 A | 4/1997 | Jones |
| 5,627,109 A | 5/1997 | Sassa et al. |
| 5,634,267 A * | 6/1997 | Farnworth et al. ............ 29/840 |
| 5,651,782 A | 7/1997 | Simon et al. |
| 5,683,592 A | 11/1997 | Bartholomew |
| 5,713,915 A | 2/1998 | Van Heugten |
| 5,728,089 A | 3/1998 | Lal et al. |
| 5,742,026 A | 4/1998 | Dickinson, Jr. |
| 5,842,387 A | 12/1998 | Marcus |
| D405,178 S | 2/1999 | Dykes |
| 5,879,326 A | 3/1999 | Godshall |
| 5,888,883 A | 3/1999 | Sasaki |
| 5,893,846 A | 4/1999 | Bales et al. |
| 5,928,161 A | 7/1999 | Krulevitch |
| 5,928,207 A | 7/1999 | Pisano |
| 5,944,717 A | 8/1999 | Lee |
| 5,972,154 A | 10/1999 | Konya |
| 5,985,217 A | 11/1999 | Krulevitch |
| 5,993,281 A | 11/1999 | Musket |
| 5,998,234 A | 12/1999 | Murata |
| 6,003,419 A | 12/1999 | Irita |
| 6,032,372 A | 3/2000 | Dischler |
| 6,056,764 A | 5/2000 | Smith |
| 6,099,543 A | 8/2000 | Smith |
| 6,117,347 A | 9/2000 | Ishida |
| 6,124,214 A | 9/2000 | Hembree |
| 6,136,724 A * | 10/2000 | Hansen et al. ............. 438/745 |
| 6,151,786 A | 11/2000 | Hellstern |
| 6,184,109 B1 | 2/2001 | Sasaki |
| 6,187,210 B1 | 2/2001 | Lebouitz |
| 6,205,993 B1 | 3/2001 | Zehavi et al. |
| 6,216,561 B1 | 4/2001 | Dischler |
| 6,250,192 B1 * | 6/2001 | Akram et al. ................. 83/495 |
| RE37,304 E | 7/2001 | Van Heugten |
| 6,253,755 B1 | 7/2001 | Wark |
| 6,256,533 B1 | 7/2001 | Yuzhakov et al. |
| 6,260,280 B1 | 7/2001 | Rapisardi |
| 6,293,270 B1 | 9/2001 | Okazaki |
| 6,294,439 B1 | 9/2001 | Sasaki |
| 6,312,212 B1 | 11/2001 | Burlew, Jr. |
| 6,312,612 B1 | 11/2001 | Sherman |
| 6,319,474 B1 | 11/2001 | Krulevitch |
| 6,325,704 B1 | 12/2001 | Brown |
| 6,327,784 B1 | 12/2001 | Altena |
| 6,334,856 B1 | 1/2002 | Allen |
| 6,358,261 B1 | 3/2002 | Chan et al. |
| 6,358,262 B1 | 3/2002 | Chan et al. |
| 6,401,580 B1 | 6/2002 | Akram et al. |
| 6,406,638 B1 | 6/2002 | Stoeber et al. |
| 6,420,245 B1 | 7/2002 | Manor |
| 6,440,096 B1 | 8/2002 | Lastovich et al. |
| 6,451,039 B1 | 9/2002 | Rickey, Jr. et al. |
| 6,482,219 B1 | 11/2002 | Bonnet |
| 6,533,949 B1 | 3/2003 | Yeshurun et al. |
| 6,554,840 B1 | 4/2003 | Matsutani et al. |
| 6,555,447 B1 | 4/2003 | Weishauss et al. |
| 6,562,698 B1 | 5/2003 | Manor |
| 6,569,175 B1 | 5/2003 | Robinson |
| 6,578,458 B1 | 6/2003 | Akram et al. |
| 6,578,567 B1 | 6/2003 | Oh et al. |
| 6,599,178 B1 | 7/2003 | Gluche et al. |
| 6,607,966 B1 | 8/2003 | Figura et al. |
| 6,615,496 B1 | 9/2003 | Fleming et al. |
| 6,623,501 B1 | 9/2003 | Heller et al. |
| 6,687,990 B1 | 2/2004 | Akram et al. |
| 6,797,621 B1 * | 9/2004 | Song et al. .................. 438/689 |
| 6,838,387 B1 * | 1/2005 | Zajac et al. .................. 738/714 |
| 2002/0020688 A1 | 2/2002 | Sherman et al. |
| 2002/0026205 A1 | 2/2002 | Matsutani et al. |
| 2002/0078576 A1 | 6/2002 | Carr et al. |
| 2002/0142182 A1 | 10/2002 | Peker et al. |
| 2002/0178883 A1 | 12/2002 | Yamamoto |
| 2002/0185121 A1 | 12/2002 | Farnworth et al. |

| | | |
|---|---|---|
| 2002/0193817 A1 | 12/2002 | Lal et al. |
| 2002/0194968 A1 | 12/2002 | Akram et al. |
| 2003/0208911 A1 | 11/2003 | Fleming et al. |

FOREIGN PATENT DOCUMENTS

| | | |
|---|---|---|
| EP | 1 092 515 A1 | 9/2000 |
| GB | 1393611 | 5/1975 |
| JP | 61210179 | 9/1986 |
| JP | 63092345 | 9/1990 |
| JP | 8085018 | 4/1996 |
| WO | WO-86/02868 | 5/1986 |
| WO | WO0057799 A1 | 10/2000 |
| WO | WO 02/062202 A2 | 8/2002 |

OTHER PUBLICATIONS

Wolf et al., Silicon Processing for the VLSI Era, vol. 1, 1986, pp. 529-531.*

Crosby, P., "Get to Know Lasers And Their Roles in Plastics", Plastics Technology, Jun. 2002.

Venkat, S., "Processing Ceramics With Lasers", Ceramic Industry, Jun. 1, 2001.

Http://hackman.mit.edu/6152J/Lecture Notes/6152J.FT01.Lecture 17-1.pdf, Lecture 17, Basics of Etching, Fall Term 2001.

* cited by examiner

5000 X

5000 X

SYSTEM AND METHOD FOR THE MANUFACTURE OF SURGICAL BLADES

CROSS REFERENCE TO RELATED APPLICATIONS

Related subject matter is disclosed in co-pending U.S. provisional patent applications, Ser. No. 60/362,999, filed Mar. 11, 2002, and Ser. No. 60/430,332, filed Dec. 3, 2002, now abandoned, the entire contents of which are expressly incorporated herein by reference.

FIELD OF THE INVENTION

The invention relates to a system and method for the manufacture of surgical instruments. More particularly, the invention relates to a system and method for the manufacture of surgical-quality blades manufactured from silicon and other crystalline materials.

BACKGROUND OF THE INVENTION

Existing surgical blades are manufactured via several different methodologies, each method having its own peculiar advantages and disadvantages. The most common method of manufacture is to mechanically grind stainless steel. The blade is subsequently honed (through a variety of different methods such as ultrasonic slurrying, mechanical abrasion and lapping) or is electrochemically polished to achieve a sharp edge. The advantage of these methods is that they are proven, economical processes to make disposable blades in high volume. The greatest disadvantage of these processes is that the edge quality is variable, in that achieving superior sharpness consistency is still a challenge. This is primarily due to the inherent limitations of the process itself. Blade edge radii can range from 30 nm to 1000 nm.

A relatively new method of blade manufacture employs coining of the stainless steel in lieu of grinding. The blade is subsequently electrochemically polished to achieve a sharp edge. This process has been found to be more economical than the grinding method. It has also been found to produce blades with better sharpness consistency. The disadvantage of this method is that the sharpness consistency is still less than that achieved by the diamond blade manufacturing process. The use of metal blades in soft tissue surgery is prevalent today due to their disposable cost and their improved quality.

Diamond blades are the gold standard in sharpness in many surgical markets, especially in the ophthalmic surgery market. Diamond blades are known to be able to cleanly cut soft tissue with minimal tissue resistance. The use of diamond blades is also desired due to their consistent sharpness, cut after cut. Most high-volume surgeons will use diamond blades since the ultimate sharpness and sharpness variability of metal blades is inferior to that of diamond. The manufacturing process used to make diamond blades employs a lapping process to achieve an exquisitely sharp and consistent edge radius. The resultant blade edge radii range from 5 nm to 30 nm. The disadvantage of this process is that it is slow and as a direct result, the cost to manufacture such diamond blades ranges from $500 to $5000. Therefore, these blades are sold for reuse applications. This process is currently used on other, less hard materials, such as rubies and sapphires, to achieve the same sharpness at a lesser cost. However, while less expensive than diamonds, ruby and/or sapphire surgical quality blades still suffer from the disadvantage that the cost of manufacture is relatively high, ranging from $50 to $500, and their edges only last through about two hundred cases. Therefore, these blades are sold for reuse and limited reuse applications.

There have been a few proposals for the manufacture of surgical blades using silicon. However, in one form or another, these processes are limited in their ability to manufacture blades in various configurations and at a disposable cost. Many of the silicon blade patents are based on anisotropic etching of silicon. The anisotropic etching process is one where the etching is highly directional, with different etch rates in different directions. This process can produce a sharp cutting edge. However, due to the nature of the process, it is limited by the blade shapes and included bevel angles that can be attained. Wet bulk anisotropic etching processes, such as those employing potassium hydroxide (KOH), ethylene-diamine/pyrcatechol (EDP) and trimethyl-2-hydroxethylammonium hydroxide (TMAH) baths, etch along a particular crystalline plane to achieve a sharp edge. This plane, typically the (111) plane in silicon <100>, is angled 54.7° from the surface plane in the silicon wafers. This creates a blade with an included bevel angle of 54.7°, which has been found to be clinically unacceptable in most surgical applications as too obtuse. This application is even worse when this technique is applied to making double bevel blades, for the included bevel angle is 109.4°. The process is further limited to the blade profiles that it can produce. The etch planes are arranged 90° to each other in the wafer. Therefore, only blades with rectangular profiles can be produced.

Thus, a need exists to manufacture blades that address the shortcomings of the methods discussed above. This system and method of the present invention can make blades with the sharpness of diamond blades at the disposable cost of the stainless steel methods. In addition, the system and method of the present invention can produce blades in high volume and with tight process control.

SUMMARY OF THE INVENTION

The above described disadvantages are overcome and a number of advantages are realized by the present invention which relates to a system and method for the manufacturing of surgical blades from a crystalline or poly-crystalline material, such as silicon, which provides for the machining of trenches in a crystalline or poly-crystalline wafer, by various means, at any desired bevel angle or blade configuration. The machined crystalline or poly-crystalline wafers are then immersed in an isotropic etching solution which uniformly removes layer after layer of molecules of the wafer material, in order to form a cutting edge of uniform radius, and of sufficient quality for soft tissue surgery applications. The system and method of the invention provides a very inexpensive means for the manufacture of such high quality surgical blades.

It is therefore an object of the invention to provide a method for manufacturing a surgical blade, comprising the steps of mounting a silicon or other crystalline or poly-crystalline wafer on a mounting assembly, machining one or more trenches on a first side of the crystalline or poly-crystalline wafer, etching the first side of the crystalline or poly-crystalline wafer to form one or more surgical blades, singulating the surgical blades, and assembling the surgical blades.

It is a further object of the invention to provide a method for manufacturing a surgical blade, comprising the steps of mounting a crystalline or poly-crystalline wafer on a mounting assembly, machining one or more trenches on a first side of the crystalline or poly-crystalline wafer, coating the first side of the crystalline or poly-crystalline wafer with a coating, dismounting the crystalline or poly-crystalline wafer from the mounting assembly, and remounting the first side of the crystalline or poly-crystalline wafer on the mounting assembly, machining a second side of the crystalline or poly-crystalline wafer, etching the second side of the crystalline or poly-crystalline wafer to form one or more surgical blades, singulating the surgical blades, and assembling the surgical blades.

It is still a further object of the invention to provide a method for manufacturing a surgical blade, comprising the steps of mounting a crystalline or poly-crystalline wafer on a mounting assembly, machining one or more trenches on a first side of the crystalline or poly-crystalline wafer, dismounting the crystalline or poly-crystalline wafer from the mounting assembly, and remounting the first side of the crystalline or poly-crystalline wafer on the mounting assembly, machining a second side of the crystalline or poly-crystalline wafer, etching the second side of the crystalline or poly-crystalline wafer to form one or more surgical blades, converting a layer of the crystalline or poly-crystalline material to form a hardened surface, singulating the surgical blades, and assembling the surgical blades.

BRIEF DESCRIPTION OF THE DRAWINGS

The novel features and advantages of the present invention will best be understood by reference to the detailed description of the preferred embodiments which follows, when read in conjunction with the accompanying drawings, in which.

DETAILED DESCRIPTION OF THE PREFERRED EMBODIMENTS

Figure 1:
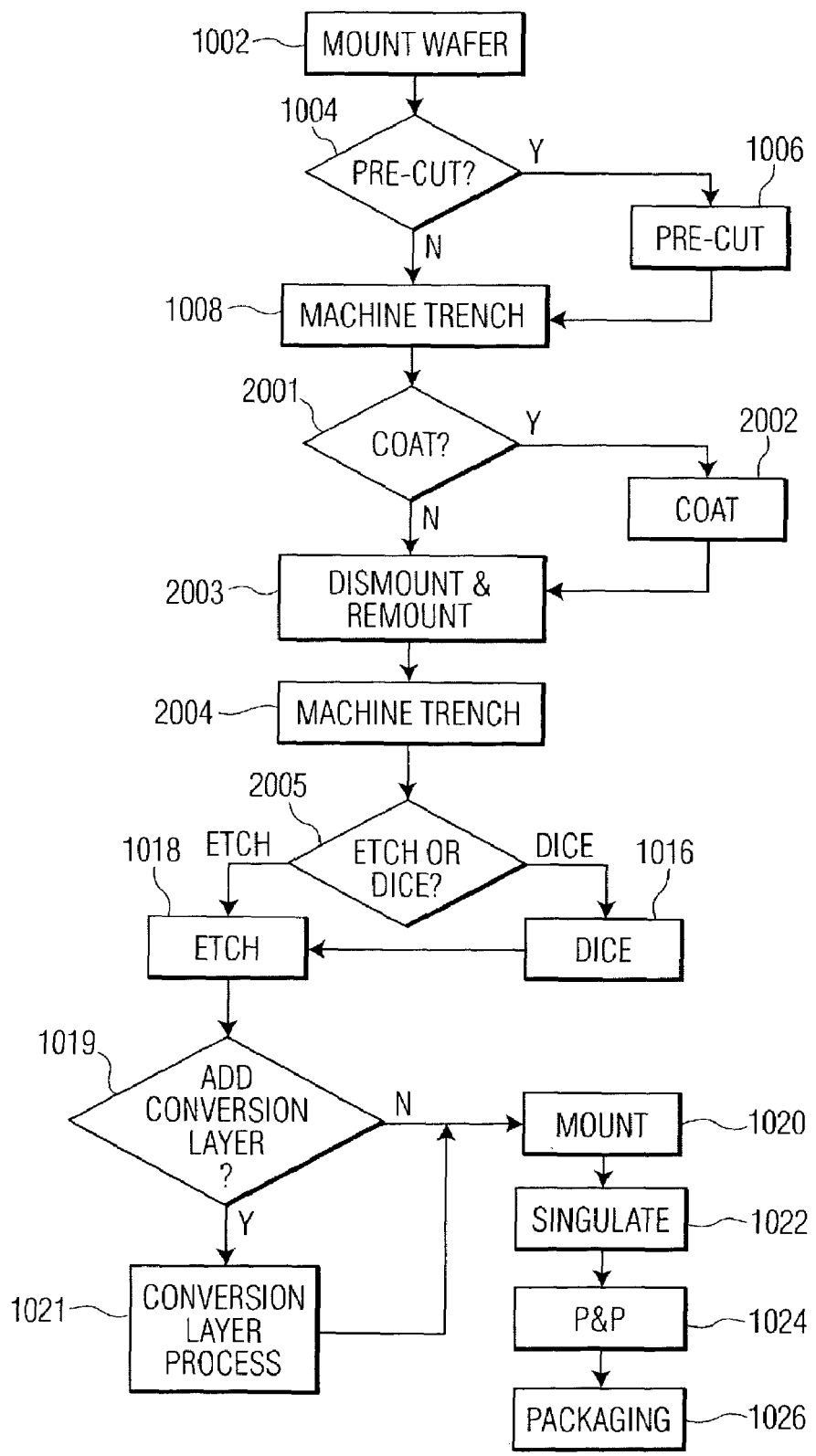
FIG. 1 illustrates a flow diagram of a method for manufacturing a double bevel surgical blade from silicon according to a first embodiment of the present invention.

The various features of the preferred embodiments will now be described with reference to the drawing figures, in which like parts are identified with the same reference characters. The following description of the presently contemplated best mode of practicing the invention is not to be taken in a limiting sense, but is provided merely for the purpose of describing the general principles of the invention.

The system and method of the present invention provides for the manufacture of surgical blades to be used for incising soft tissue. Although the preferred embodiment is shown to be a surgical blade, numerous cutting devices can also be fabricated in accordance with the methods discussed in detail below. Therefore, it will be apparent to one skilled in the art of the invention that although reference is made to "surgical blades" throughout these discussions, numerous other types of cutting devices can be fabricated, including, for example, medical razors, lancets, hypodermic needles, sample collection cannula and other medical sharps.

The preferred base material that the blades will be manufactured from is crystalline silicon with a preferred crystal orientation. However, other orientations of silicon are suitable, as well as other materials that can be isotropically etched. For example, silicon wafers with orientation <110> and <111> can also be used, as well as silicon wafers doped at various resistivity and oxygen content levels. Also, wafers made of other materials can be used, such as silicon nitride and gallium arsenide. Wafer form is the preferred format for the base material. In addition to crystalline materials, poly-crystalline materials can also be used to manufacture surgical blades. Examples of these poly-crystalline materials include polycrystalline silicon. It will be understood that the term "crystalline" as used herein will be used to refer to both crystalline and poly-crystalline materials.

Therefore, it will be apparent to one skilled in the art of the invention that although reference is made to "silicon wafers" throughout these discussions, any of the aforementioned materials in combination with various orientations can be used in accordance with the various embodiments of the present invention, as well as other suitable materials and orientations that might become available.

Figure 2:
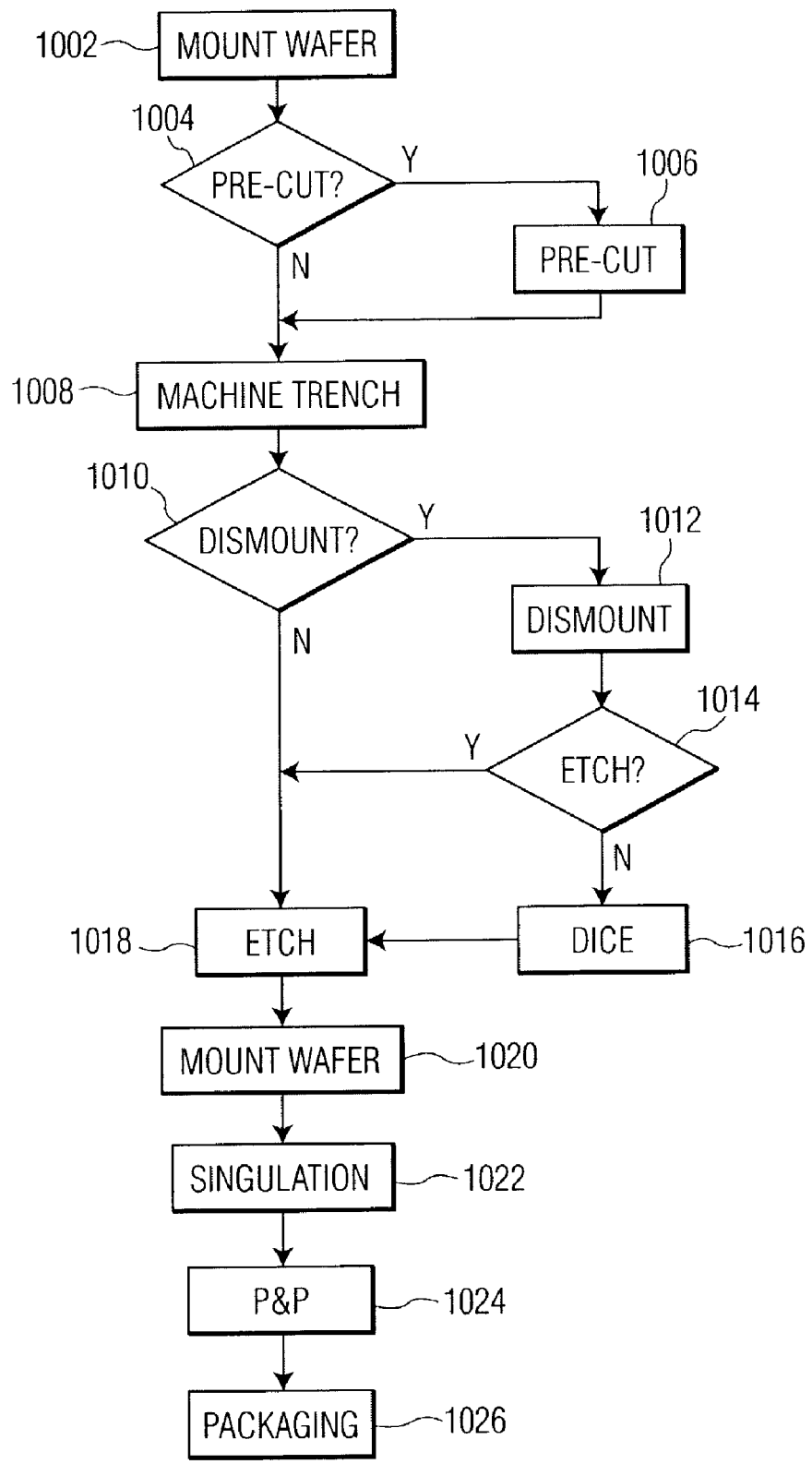
FIG. 2 illustrates a flow diagram of a method for manufacturing a single bevel surgical blade from silicon according to a second embodiment of the present invention.
Figure 3:
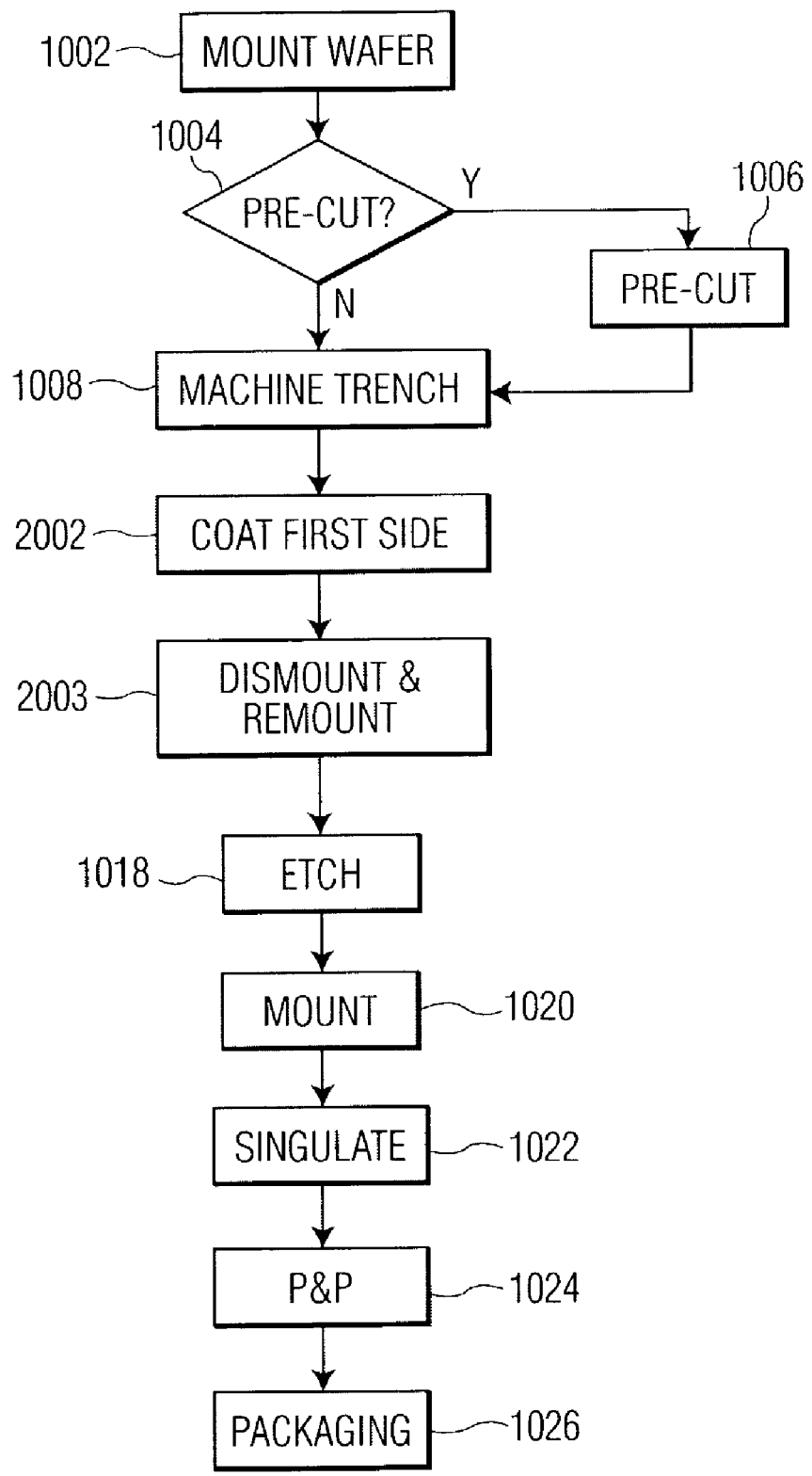
FIG. 3 illustrates a flow diagram of an alternative method for manufacturing a single bevel surgical blade from silicon according to a third embodiment of the present invention.

FIG. 1 illustrates a flow diagram of a method for manufacturing a double bevel surgical blade from silicon according to a first embodiment of the present invention. The method of FIGS. 1, 2 and 3 describe generally processes which can be used to manufacture silicon surgical blades according to the present invention. However, the order of the steps of the method illustrated in FIGS. 1, 2 and 3 can be varied to create silicon surgical blades of different criteria, or to meet different manufacturing environments. As such, the method of FIGS. 1, 2 and 3 are meant to be representative of general embodiments of the method according to the present invention, in that there are many different permutations which include the same steps that can result in a manufactured silicon surgical blade in accordance with the spirit and scope of the present invention.

Figure 4:
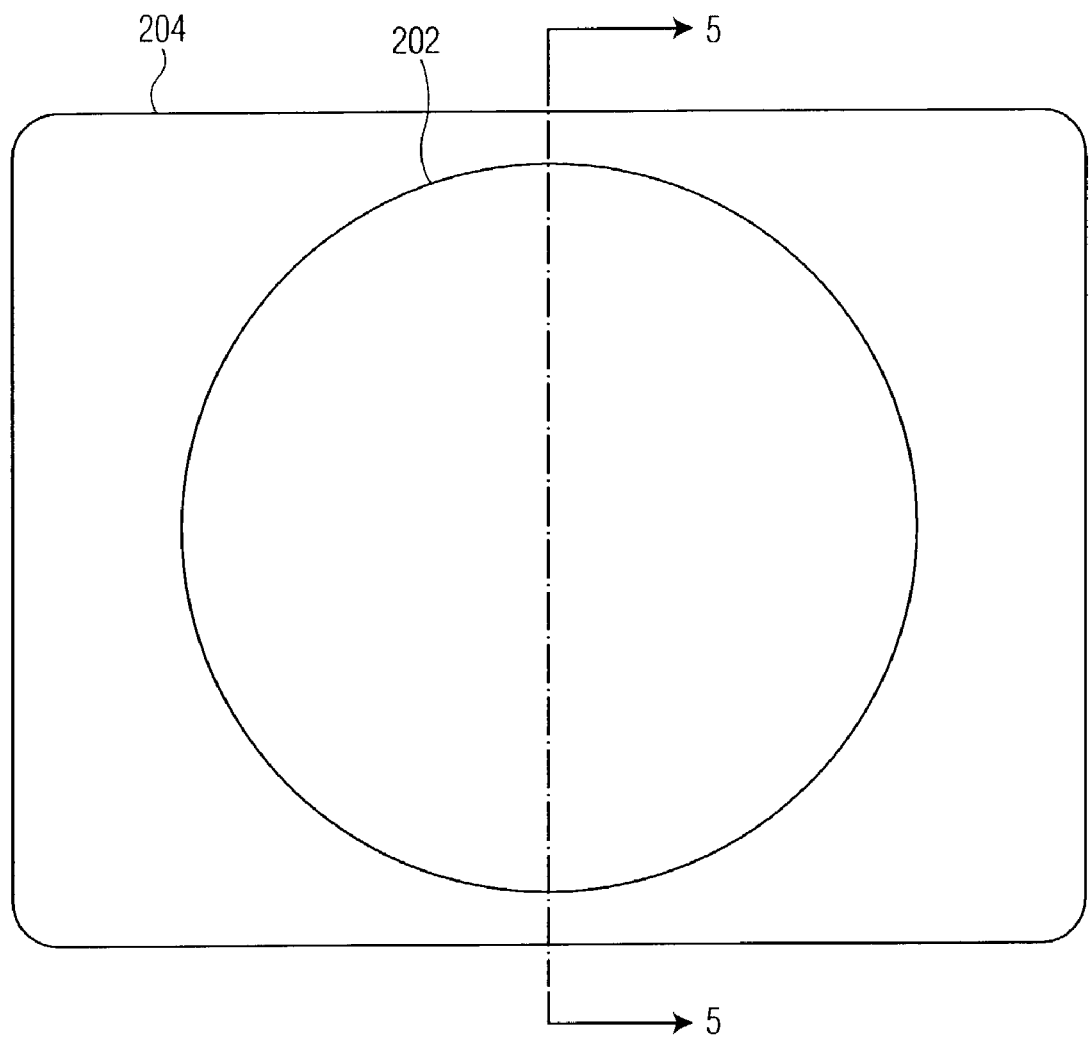
FIG. 4 illustrates a silicon wafer mounted on a mounting assembly, top view.
Figure 5:
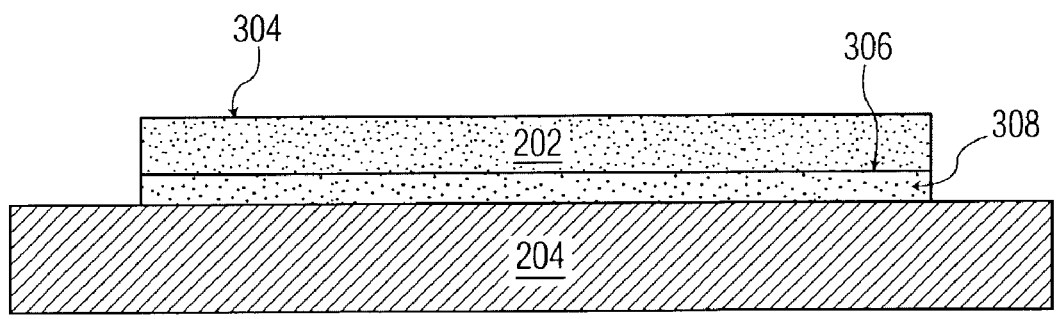
FIG. 5 illustrates a silicon wafer mounted on a mounting assembly with tape, side view.

The method of FIG. 1 is used to manufacture a double bevel surgical blade, preferably with a crystalline material such as silicon, in accordance with an embodiment of the invention, and begins with step 1002. In step 1002, the silicon wafer is mounted on mounting assembly 204. In FIG. 4, the silicon wafer 202 is shown mounted on a wafer frame/UV tape assembly (mounting assembly) 204. The mounting assembly 204 is a common method to handle silicon wafer material in the semiconductor industry. One skilled in the art can appreciate that mounting the silicon (crystalline) wafer 202 upon a wafer mounting assembly 204 is not necessary for the manufacture of surgical blades according to the preferred embodiments of the invention FIG. 5 illustrates the same silicon wafer 202 mounted on the same mounting assembly 204 but in a side view (left or right; it is symmetrical, though that need not be the case). In FIG. 5, silicon wafer 202 is mounted on tape 308 which is then mounted on mounting assembly 204. Silicon wafer 202 has a first side 304 and a second side 306.

Figure 6:
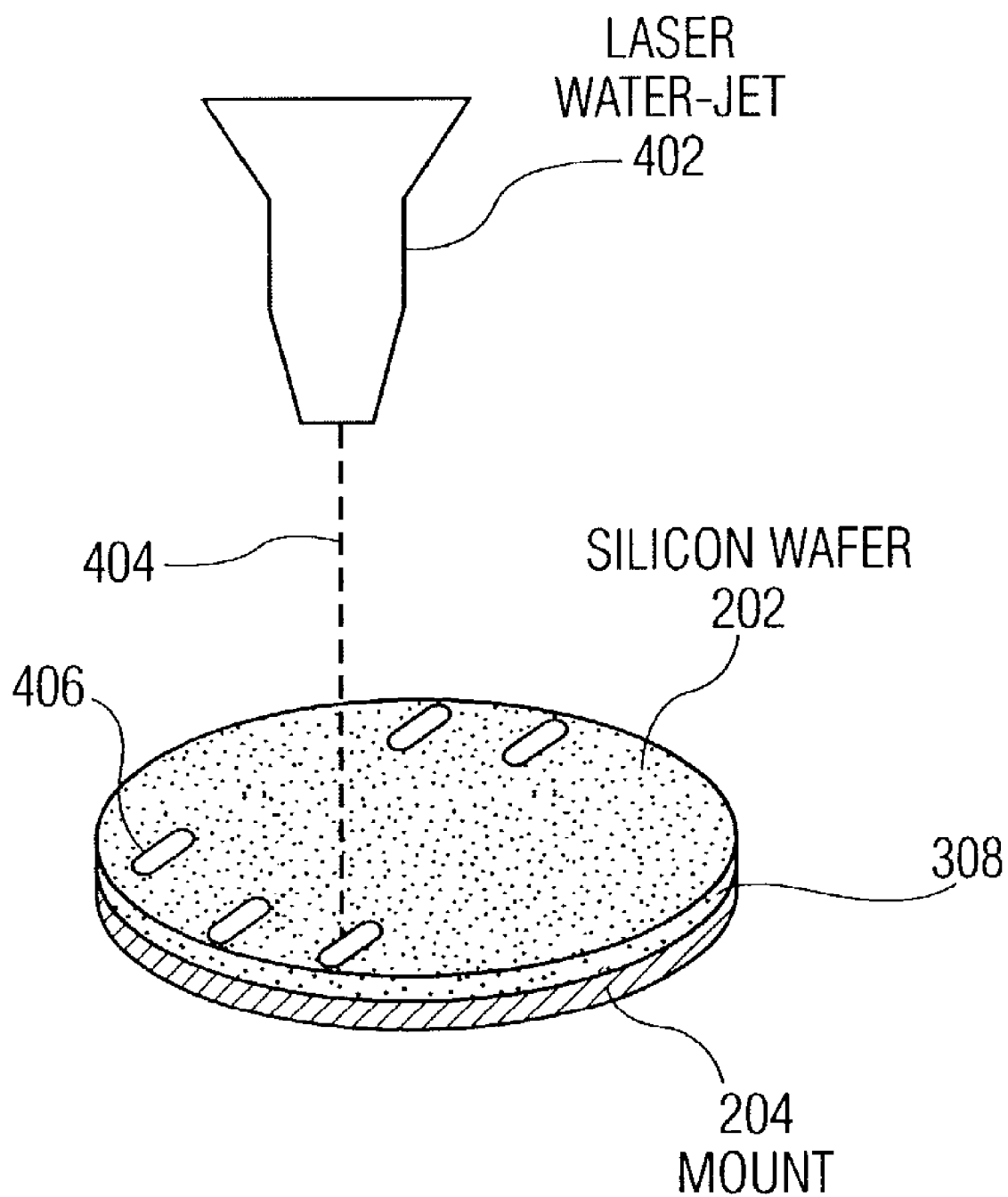
FIG. 6 illustrates the use of a laser waterjet for pre-cutting a silicon wafer to assist in the machining of trenches in the silicon wafer according to an embodiment of the present invention.

Referring again to FIG. 1, decision step 1004 follows step 1002. Decision step 1004 determines whether an optional pre-cut is to be made in silicon wafer 202, in step 1006, if so desired. This pre-cut can be performed by a laser waterjet 402, as shown in FIG. 6. In FIG. 6, laser waterjet 402 is shown directing laser beam 404 onto silicon wafer 202, which is mounted on mounting assembly 204. As can be seen in FIG. 6, various pre-cut holes (or through-hole fiducials) 406 can be created in silicon wafer 202 as a result of the impact of the laser beam 404 with silicon wafer 202.

Silicon wafer 202 is ablated by the laser beam 404 upon silicon wafer 202. The ability of the laser beam 404 to ablate the silicon wafer 202 is related to the laser's wavelength $\lambda$. In the preferred embodiment, which uses a silicon wafer, the wavelength that yields the best results is 1064 nano-meters, typically provided by a YaG laser, though other types of lasers can be used as well. If a different crystalline or poly-crystalline material is used, then other wavelengths and laser types will be more appropriate.

The resultant through-hole fiducials 406 (a plurality of holes can be cut in this manner) can be used as guides for machining trenches (discussed in detail with respect to step 1008 below), especially if a dicing saw blade is to be used to machine the trenches. Through-hole fiducials 406 can also be cut by any laser beam (e.g., an excimer laser or laser waterjet 402) for the same purpose. The pre-cut through-hole fiducials are typically cut in the shape of a plus "+" or a circle. However, the choice of through-hole fiducial shape is directed by the specific manufacturing tools and environment, and thus need not be limited to just the two aforementioned shapes.

In addition to the use of a laser beam to pre-cut through-hole fiducials, other mechanical machining methods can also be used. These include, for example, but are not limited to, drilling tools, mechanical grinding tools and an ultra-sonic machining tool 100. While use of the devices is novel with respect to the preferred embodiments of the invention, the devices and their general use are well known to those skilled in the art.

Precutting can be performed to silicon wafer 202 prior to machining trenches in order for silicon wafer 202 to maintain its integrity and not fall apart during the etching process. A laser beam (e.g., a laser waterjet 402 or excimer laser) can be used to scroll in elliptical through-hole slots for the dicing blade 502 (discussed in detail in reference to FIGS. 7A–7C) to begin machining trenches in silicon wafer 202 within its perimeter. The mechanical machining devices and methods (discussed above) used to create the through-hole fiducials can also be used to create the through-hole slots as well.

Referring again to FIG. 1, the next step is step 1008, which can follow either step 1006 (if through-hole fiducials 406 are cut into silicon wafer 202), or steps 1002 and 1004, which is the silicon wafer mounting step ("step" 1004 is not a physical manufacturing step; these decision steps are included to illustrate the total manufacturing process and its variances). In step 1008, trenches are machined into first side 304 of silicon wafer 202. There are several methods that can be used to machine the trenches, dependent on manufacturing conditions and the desired design of the finished silicon surgical blade product.

The methods for machining can employ either a dicing saw blade, laser system, an ultrasonic machining tool or a hot-forging process. Other methods for machining can also be used. Each will be discussed in turn. The trench that is machined by any of these methods provides the angle (bevel angle) of the surgical blade. As the trench machine operates on silicon wafer 202, silicon material is removed, either in the shape of the dicing saw blade, the pattern formed by the excimer laser, or the pattern formed by an ultrasonic machining tool, in the desired shape of the surgical blade preform. In the case of a dicing saw blade, the silicon surgical blades will have only straight edges; in the latter two methods, the blades can be essentially any shape desired. In the case of a hot-forging process, the silicon wafer is heated to make it malleable, then pressed between two die, each one having a three dimensional form of the desired trenches to be "molded" into the heated, malleable silicon wafer. For purposes of this discussion, "machining" trenches encompasses all methods of manufacturing trenches in a silicon wafer, including those mentioned specifically, whether by a dicing saw blade, excimer laser, ultrasonic machine or a hot-forging process, and equivalent methods not mentioned. These methods of machining the trenches will now be discussed in detail.

Figure 7A:
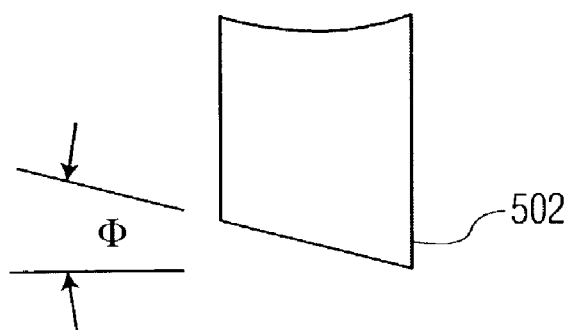
FIGS. 7A–7D illustrate dicing saw blade configurations used to machine trenches in a silicon wafer according to an embodiment of the present invention.
Figure 7B:
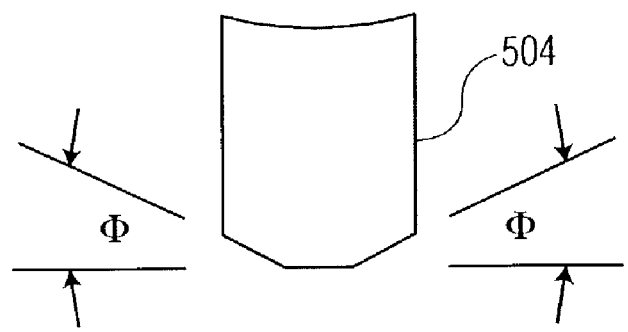
Figure 7C:
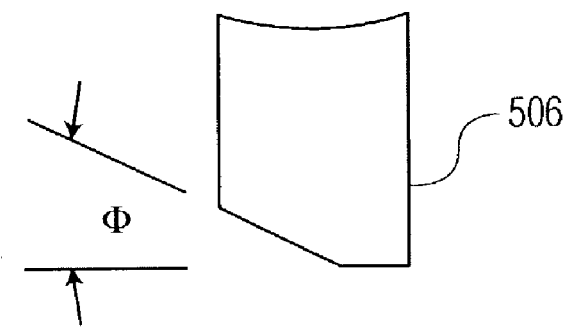
Figure 7D:
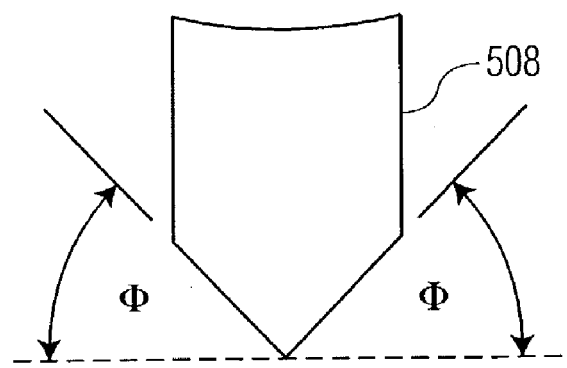

FIGS. 7A–7D illustrate dicing saw blade configurations used to machine trenches in a silicon wafer according to an embodiment of the invention. In FIG. 7A, first dicing saw blade 502 exhibits angle Φ which will essentially be the resulting angle of the surgical blade after the entire manufacturing process has been completed. FIG. 7B illustrates second dicing saw blade 504, with two angled cutting surfaces, each exhibiting a cutting angle Φ. FIG. 7C illustrates third dicing saw blade 506 which also has cutting angle Φ, but has a slightly different configuration than that of first dicing saw blade 502. FIG. 7D illustrates a fourth dicing saw blade 508 with two angled cutting surfaces, similar to FIG. 7B, each exhibiting a cutting angle Φ.

Although each of the dicing saw blades 502, 504, 506 and 508 illustrated in FIGS. 7A–7D have the same cutting angle Φ, it will be apparent to one skilled in the art that the cutting angle can be different for different uses of the silicon based surgical blades. In addition, as will be discussed below, a single silicon surgical blade can have different cutting edges with different angles included therein. Second dicing saw blade 504 can be used to increase the manufacturing capacity for a particular design of a silicon based surgical blade, or, produce silicon surgical blades that have two or three cutting edges. Various examples of blade designs will be discussed in detail in reference to FIGS. 20A–20G. In a preferred embodiment of the invention, the dicing saw blade will be a diamond grit saw blade.

A special dicing saw blade is used to machine channels in the first side 304 of the silicon wafer 202. The dicing saw blade composition is specifically chosen to provide the best resultant surface finish while maintaining acceptable wear life. The edge of the dicing saw blade is shaped with a profile that will shape the resultant channel in silicon wafer 202. This shape will correlate to the resultant blade bevel configuration. For instance, surgical blades typically have included bevel angles that range from 15° to 45° for single bevel blades and half included bevel angles that range from 15° to 45° for double bevel blades. Selection of a dicing saw blade in conjunction with etch conditions provides precise control of bevel angle.

Figure 8:
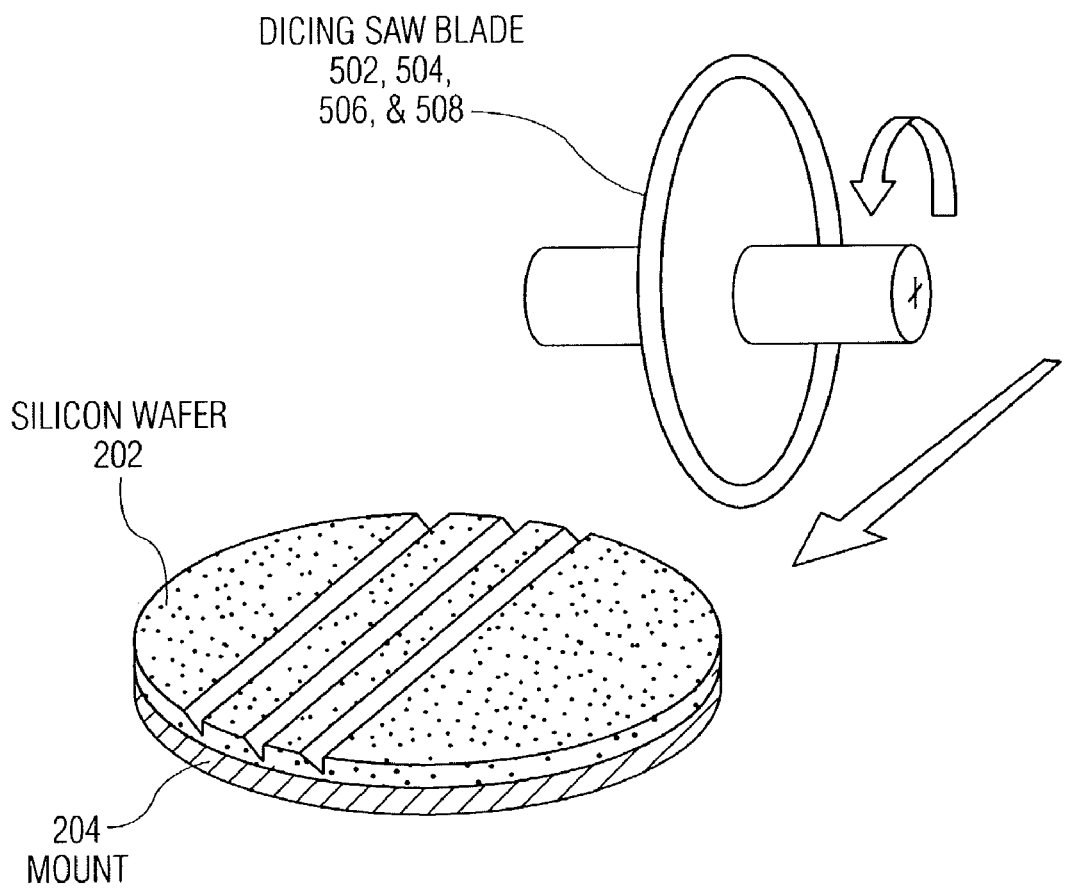
FIG. 8 illustrates the operation of a dicing saw blade through a silicon wafer mounted on support backing according to an embodiment of the present invention.
Figure 9:
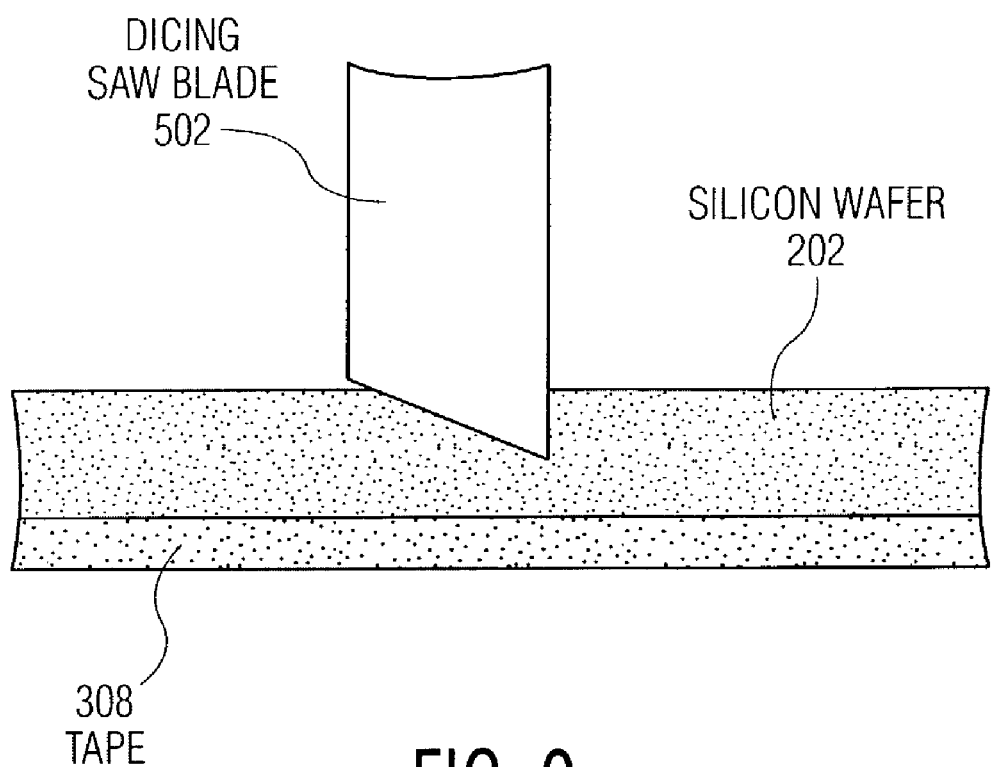
FIG. 9 illustrates a cross-section view of a dicing saw blade machining a trench in a silicon wafer that is tape mounted according to an embodiment of the present invention.
Figure 10A:
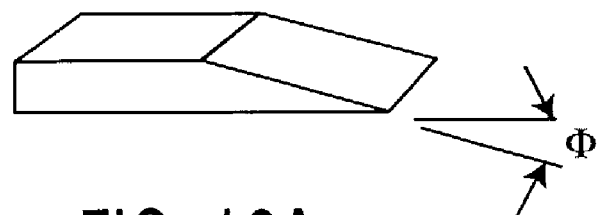
FIGS. 10A and 10B illustrate a silicon surgical blade with a single bevel cutting edge and a silicon surgical blade with a double bevel cutting edge respectively, made in accordance with an embodiment of the present invention.
Figure 10B:
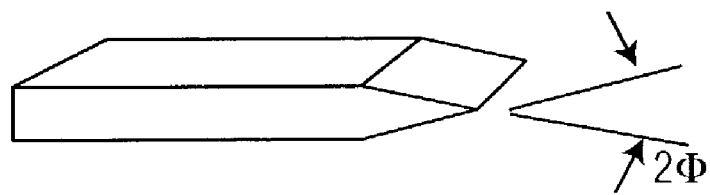

FIG. 8 illustrates the operation of a dicing saw blade through a silicon wafer mounted on support backing according to an embodiment of the invention. FIG. 8 illustrates the operation of a dicing saw blade machine that is machining trenches in first side 304 of silicon wafer 202. In this example, any of the dicing saw blades of FIGS. 7A–7D (502, 504, 506 or 508) can be used to create the silicon based surgical blade edges. It should also be understood that the blade configurations of FIGS. 7A–7D are not the only possible configurations that can be created for dicing saw blades. FIG. 9 illustrates a cross section view of a dicing saw blade machining a trench in a silicon wafer that is tape mounted according to an embodiment of the invention. FIG. 9 illustrates a close up cross section view of the same dicing saw blade assembly shown in FIG. 8 actually penetrating silicon wafer 202. It can be seen that dicing saw blade 502 does not penetrate all the way through silicon wafer 202, but, for a single bevel cut, penetrates approximately 50–90% of the thickness of silicon wafer 202. This applies to any method used for machining (or molding, via hot-forging) a single bevel trench. For a double bevel cut by any dicing saw blade, or, any of the machining methods, approximately 25–49% of the thickness of silicon wafer 202 will be machined away (or molded) on each side of silicon wafer 202. FIGS. 10A and 10B illustrate a silicon surgical blade with a single bevel cutting edge and a silicon surgical blade with a double bevel cutting edge respectively, made in accordance with an embodiment of the invention.

Figure 8A:
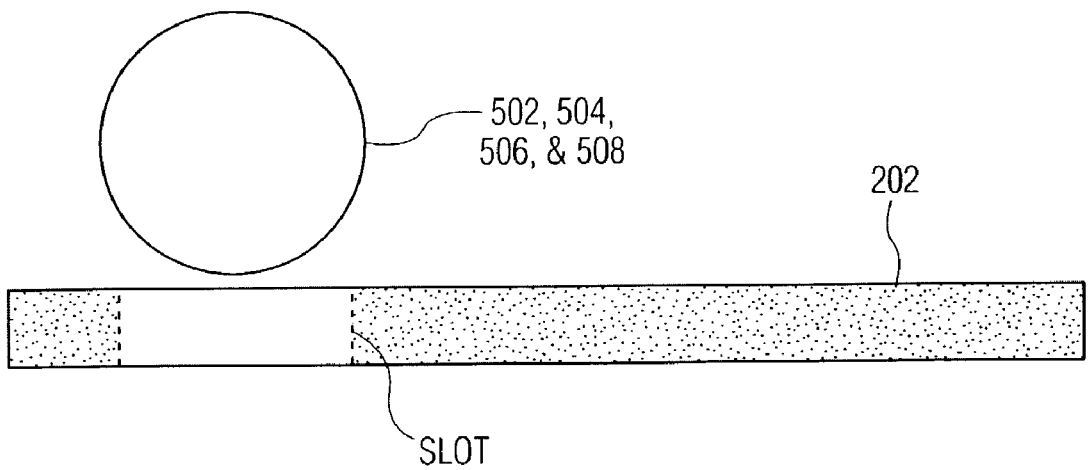
FIGS. 8A–8C illustrate a use of slots when machining trenches in a silicon wafer with a dicing saw blade according to an embodiment of the invention.
Figure 8B:
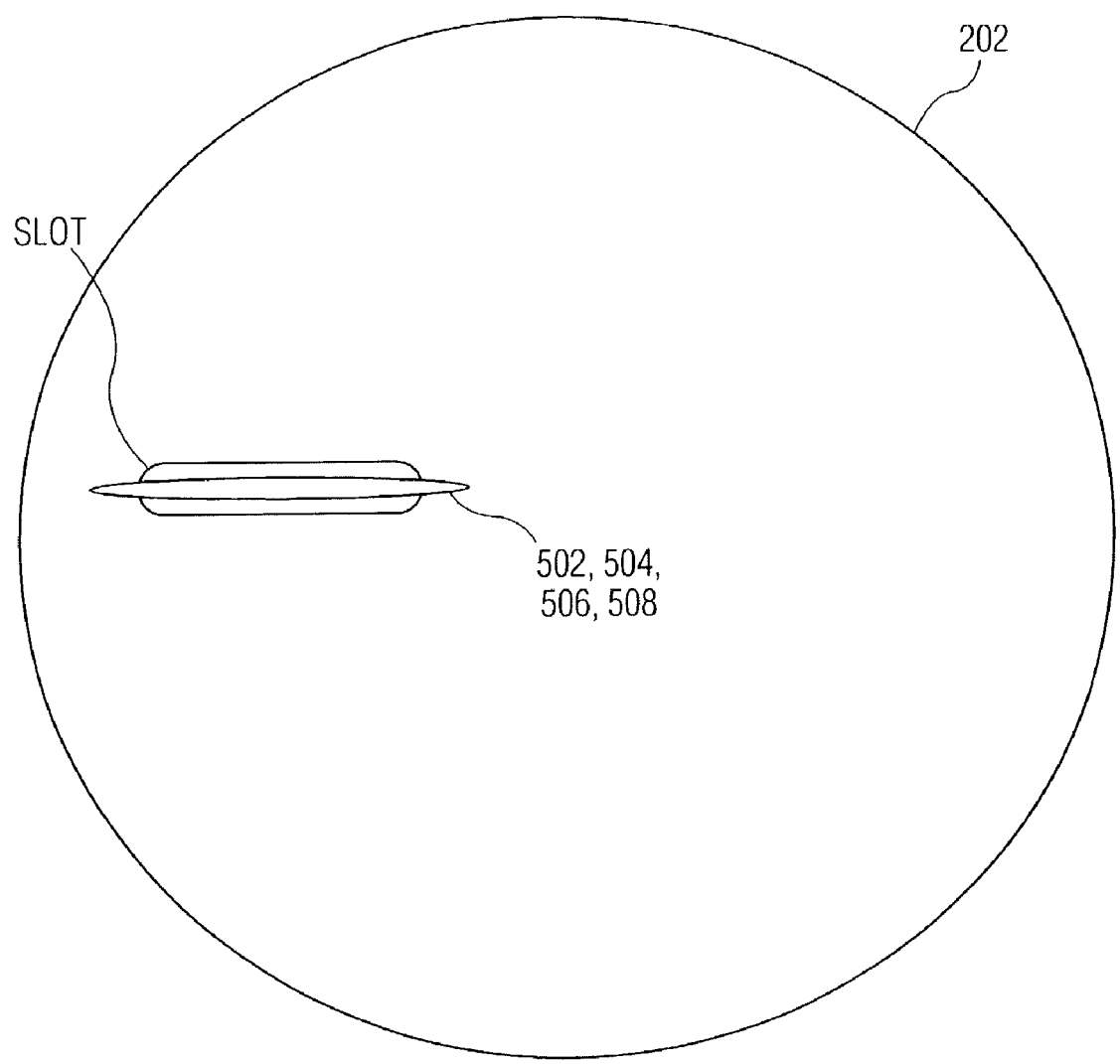
Figure 8C:
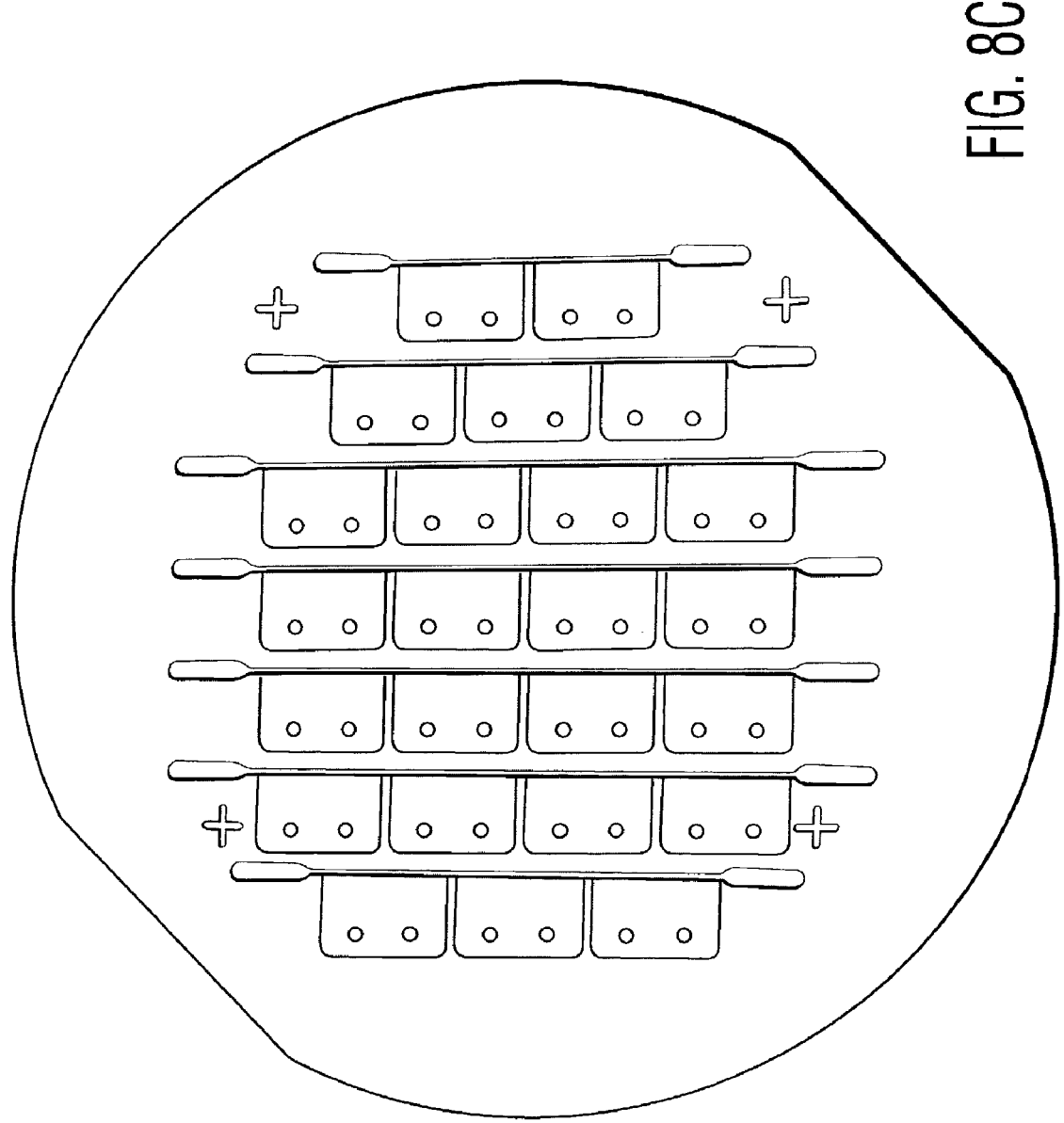

As discussed above, slots can also be cut into the silicon wafer 202, especially if a dicing saw blade will be used to machine the trenches. Slots can be cut into the silicon wafer 202 in a fashion similar to the through-hole fiducials, i.e., with the laser water-jet or excimer laser, but serve a very different purpose. Recall that the through-hole fiducials are used by the trench machine in order to accurately position the silicon wafer 202 on the trench machine. This is especially useful when making double bevel blades, because the second machining (on the opposite side of the silicon wafer 202) must be accurately positioned to ensure a properly manufactured double bevel blade. Slots, however, are used for a different purpose. Slots allow the dicing saw blade to begin cutting the silicon wafer 202 away from the edge (as shown in FIG. 8), without splintering or breaking the silicon wafer 202. This is the preferred embodiment, as is shown in FIG. 8A. Referring to FIG. 8, it is apparent that if slots are not used, and the trenches are machined as shown, the machined silicon wafer 202 will be susceptible to breakage along the machined trenches because the silicon wafer is significantly thinner in those areas, and small stresses can cause it to break. That is, the machined silicon wafer of FIG. 8 lacks structural rigidity. Compare this to the silicon wafer of FIG. 8C. The machined silicon wafer 202 of FIG. 8C is much more rigid and leads to improved manufacturing throughput. Fewer silicon wafers 202 machined according to FIG. 8C will break than those of FIG. 8. As shown in FIGS. 8A and 8B, the slot is made wider than the dicing saw blade, and long enough to allow the dicing saw blade to be inserted into it to begin machining at the proper depth. Therefore, the dicing saw blade does not attempt to cut the silicon wafer 202 while it is moving downward, which causes splintering and breakage; the dicing saw blade begins to cut when it is moving in an horizontal manner, as it was designed to do. FIG. 8C illustrates a series of slots and machined trenches in a first side of a silicon wafer 202.

Figure 11:
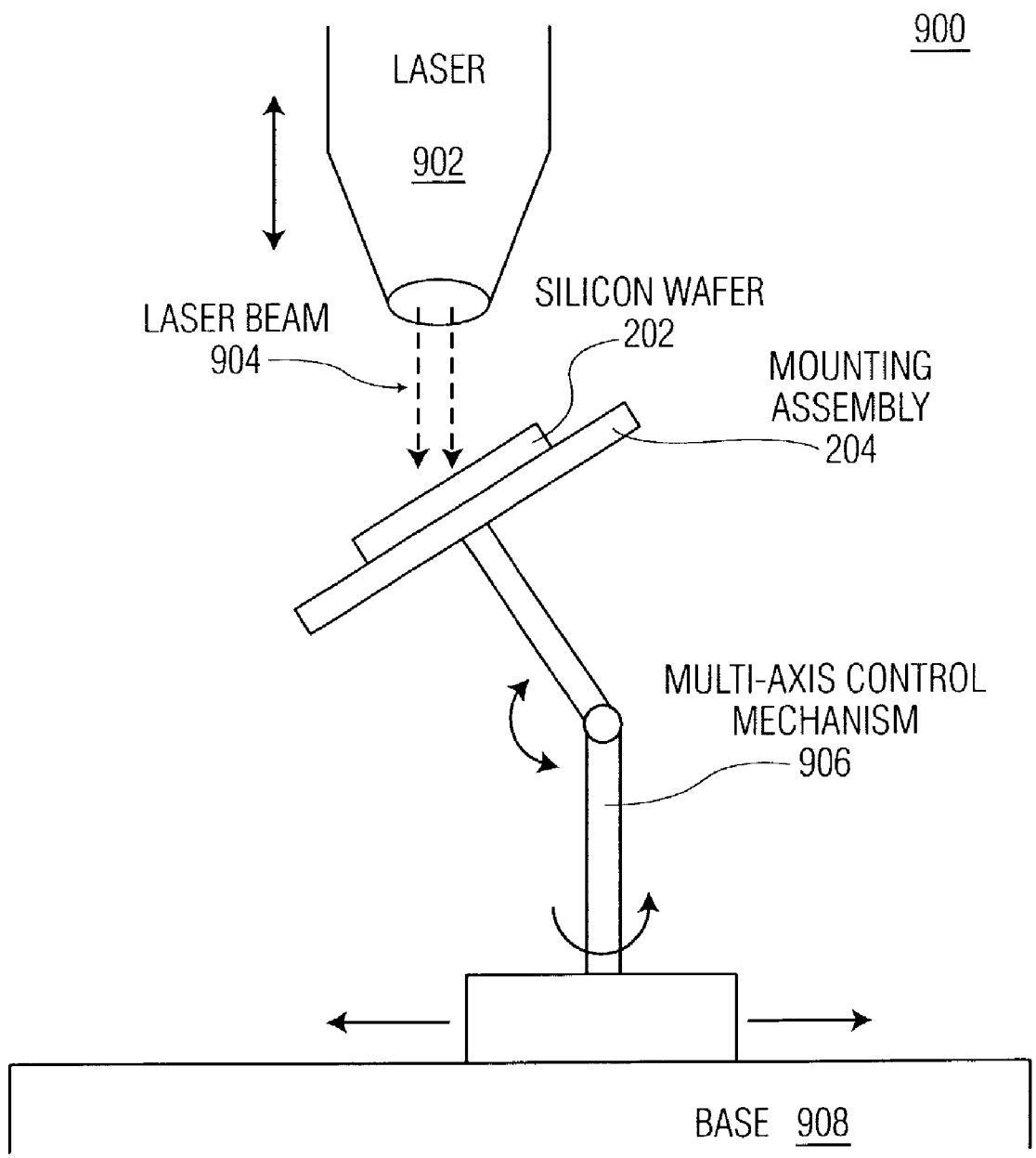
FIG. 11 illustrates a block diagram of a laser system used to machine trenches in a silicon wafer according to an embodiment of the present invention.

FIG. 11 illustrates a block diagram of a laser system used to machine trenches in a silicon wafer according to an embodiment of the invention. The trenches can also be ultrasonically machined as described in reference to FIG. 12, discussed in detail below. The advantage of these two methods is that blades can be manufactured with non-linear and complex cutting edge profiles, e.g. crescent blades, spoon blades, and scleratome blades. FIG. 11 illustrates a simplified laser machine assembly 900. The laser machine assembly 900 is comprised of a laser 902, which emits a laser beam 904, and a multi-axis control mechanisim 906 which rests on base 908. Of course, the laser machine assembly 900 can also comprise a computer, and possibly a network interface, which have been omitted for clarity.

When machining trenches with the laser machine assembly 900, the silicon wafer 202 is mounted on the mounting assembly 204 which also is adaptable to be manipulated by multi-axis control mechanisism 906. Through the use of laser machining assembly 900 and various light beam masking techniques, an array of blade profiles can be machined. The light beam mask is located inside laser 902, and through careful design, prevents laser 902 from ablating silicon material where it is not intended. For double bevel blades, the opposing side is machined the same way using the pre-cut chamfers 206A, 206B or fiducials 406 for alignment.

Laser 902 is used to accurately and precisely machine trench patterns (also referred to as an "ablation profile" in reference to use of a laser) into either first side 304 or second side 306 of silicon wafer 202 in preparation of the wet isotropic etching step (which is discussed in detail with reference to FIG. 1, step 1018). Multi-axis control and the use of internal laser light beam masks are used to raster the aforementioned ablation profiles in silicon wafer 202. As a result, a contoured trench is achieved that has shallow angled slopes that correspond to that which is required for the surgical blade product. Various curvilinear profile patterns can be achieved via this process. There are several types of lasers that can be used in this machining step. For example, an excimer laser or laser waterjet 402 can be used. The wavelength of the excimer laser 902 can range between 157 nm and 248 nm. Other examples include a YaG laser and lasers with a wavelength of 355 nanometers. Of course, one skilled in the art can appreciate that laser beams with certain wavelengths within the range of 150 nm to 11,000 nm can be used to machine trench patterns.

Figure 12:
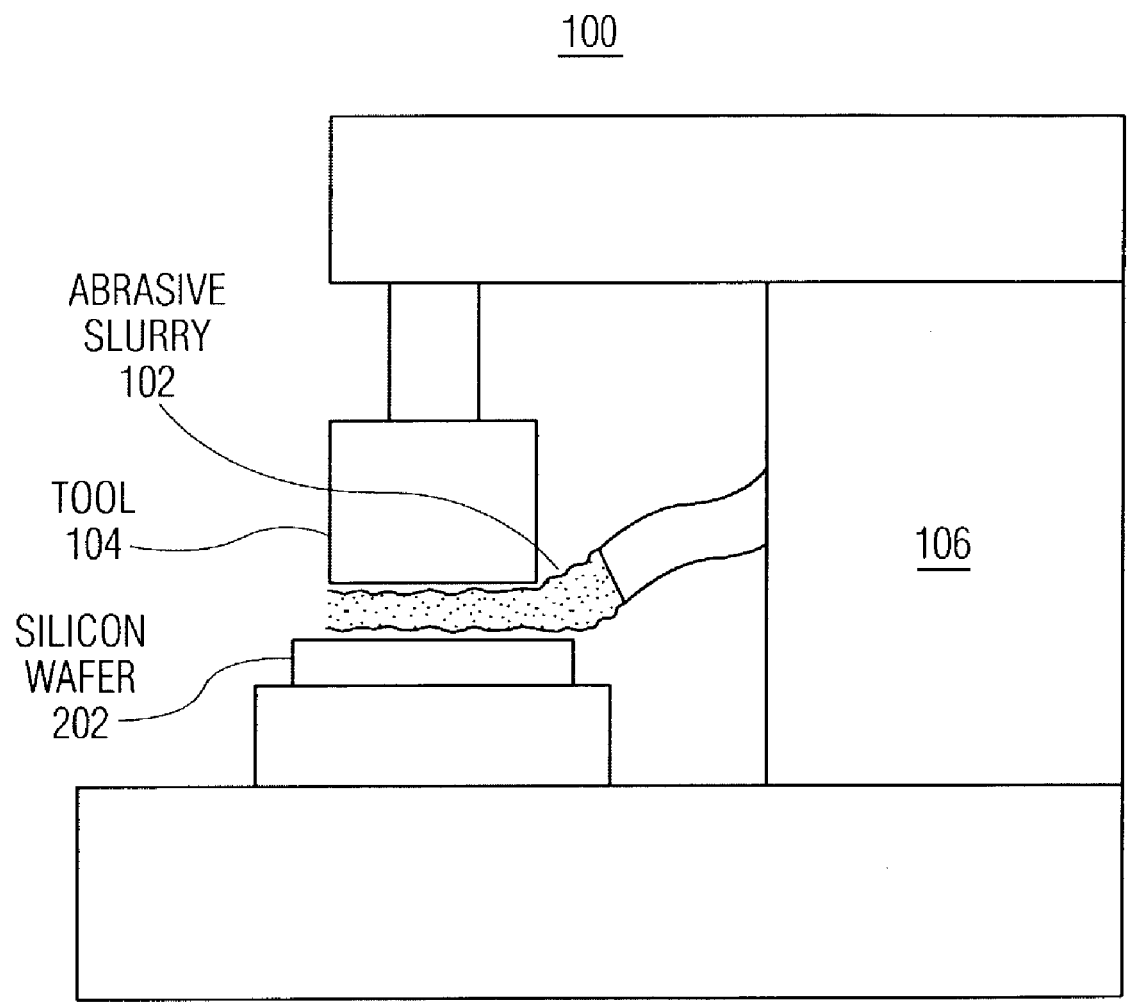
FIG. 12 illustrates a block diagram of an ultrasonic machining system used to machine trenches in a silicon wafer according to an embodiment of the present invention.

FIG. 12 illustrates a block diagram of an ultrasonic machining system used to machine trenches in a silicon wafer according to an embodiment of the present invention. Ultrasonic machining is performed by using a precisely machined ultrasonic tool 104 that is then used to machine, with abrasive slurry 102, first side 304 or second side 306 of silicon wafer 202. The machining is done to one side at a time. For double bevel blades, the opposing side is machined the same way using the through-hole fiducials 406 for alignment.

Ultrasonic machining is used to accurately and precisely machine trench patterns into the silicon wafer 202 surface in preparation for the wet isotropic etching step. Ultrasonic machining is performed by ultrasonically vibrating a mandrel/tool (tool) 104. Tool 104 does not come in contact with silicon wafer 202, but is in close proximity to silicon wafer 202 and excites abrasive slurry 102 by operation of ultrasonic waves emitted by tool 104. The ultrasonic waves emitted by tool 104 force abrasive slurry 102 to erode silicon wafer 202 to the corresponding pattern that is machined on tool 104.

Tool 104 is machined, via milling, grinding or electrostatic discharge machining (EDM), to create the trench pattern. The resultant pattern on the machined silicon wafer 202 corresponds to that which was machined on tool 104. The advantage of using an ultrasonic machining method over an excimer laser is that an entire side of silicon wafer 202 can have numerous blade trench patterns ultrasonically machined at the same time. Thus, the process is fast and relatively inexpensive. Also, like the excimer laser machining process, various curvilinear profile patterns can be achieved via this process.

Figure 13:
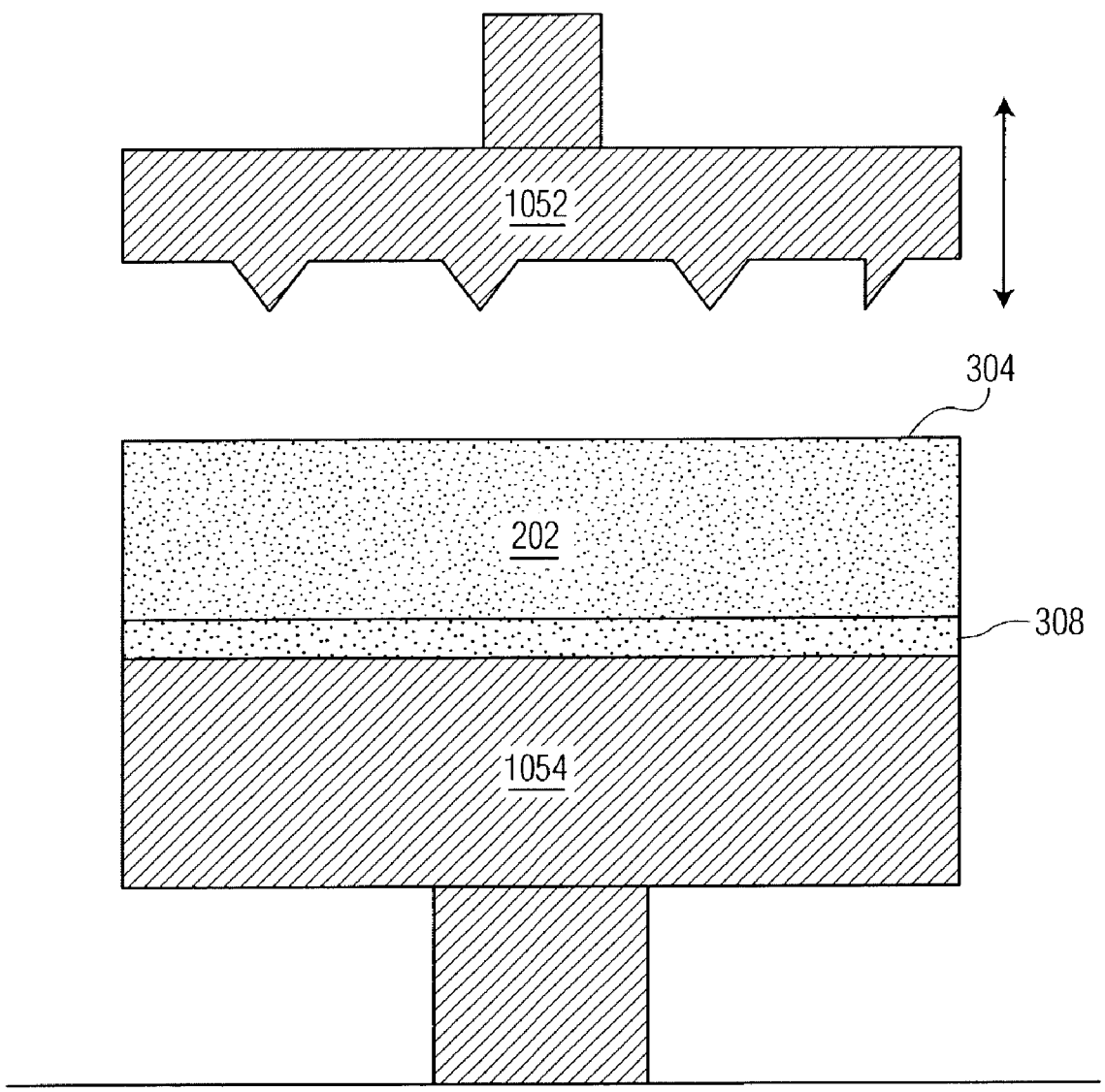
FIG. 13 illustrates a diagram of a hot-forging system used to form trenches in a silicon wafer according to an embodiment of the present invention.

FIG. 13 illustrates a diagram of a hot-forging system used to form trenches in a silicon wafer according to an embodiment of the invention. The trench configurations can also be hot forged into the wafer surface. This process employs heating the wafer to a malleable condition. The wafer surfaces are subsequently pressed between two die that incorporate the negative pattern to that of the resultant trenches.

Silicon wafer 202 is pre-heated in a heat chamber, or can be heated completely by operation of heated base member 1054, upon which silicon wafer 202 sits. After sufficient time at elevated temperatures has passed, silicon wafer 202 will become malleable. Then, heated die 1052 is forced down upon silicon wafer 202 with sufficient pressure to impress the negative image of heated die 1052 into first side 304 of silicon wafer 202. The design of die 1052 can be such that there are numerous trenches of various bevel angles, depths, lengths and profiles, in order to create virtually any blade design imaginable. The diagram illustrated in FIG. 13 is greatly simplified and exaggerated to clearly show the pertinent features of the hot-forging process.

Figure 14:
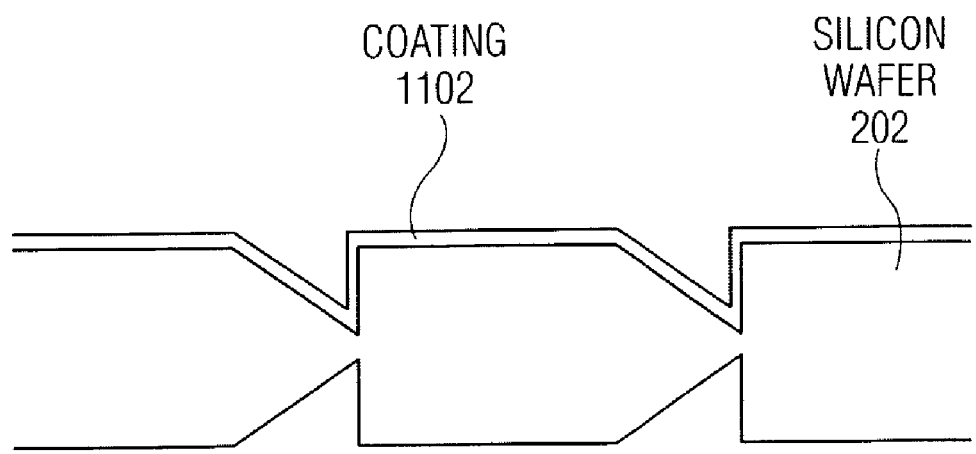
FIG. 14 illustrates a silicon wafer with a single machined trench with a coating applied to the machined side according to an embodiment of the present invention.

Having discussed the several methods for machining trenches, attention is again redirected to FIG. 1. Following step 1008, in which the trenches are machined into first side 304 of silicon wafer 202, a decision must be made, in decision step 2001, as to whether to coat the silicon wafer 202. FIG. 14 illustrates a silicon wafer with a single machined trench with a coating applied to the machined side, according to an embodiment of the present invention. If a coating is to be applied, then coating 1102 can be applied to first side 304 of silicon wafer 202 in step 2002 according to one of many techniques known to those skilled in the art of the invention. Coating 1102 is supplied to facilitate etching control and to provide additional strength to the resultant blade edge. Silicon wafer 202 is placed in a deposition chamber where the entire first side 304 of silicon wafer 202—including the flat area and the trenched area—is coated with a thin layer of silicon nitride ($Si_3N_4$). The resultant coating 1102 thickness can range from 10 nm to 2 microns. The coating 1102 can be comprised of any material that is harder than the silicon (crystalline) wafer 202. Specifically, coating 1102 can also be comprised of titanium nitride (TiN), aluminum titanium nitride (AlTiN), silicon dioxide ($SiO_2$), silicon carbide (SiC), titanium carbide (TiC), boron nitride (BN) or diamond-like-crystals (DLC). Coatings for double bevel surgical blades will be discussed again in greater detail below, in reference to FIGS. 18A and 18B.

After coating 1102 has been applied in optional step 2002, the next step is step 2003, dismounting and remounting (step 2003 can also follow step 1008 if no coating was applied). In step 2003, silicon wafer 202 is dismounted from tape 308 utilizing the same standard mounting machine. The machine dismounts silicon wafer 202 by radiating ultra-violet (UV) light onto the UV sensitive tape 308 to reduce its tackiness. Low tack or heat release tape can also be used in lieu of UV sensitive tape 308. After sufficient UV light exposure, silicon wafer 202 can be easily lifted from the tape mounting. Silicon wafer 202 is then remounted, with second side 306 facing up, in preparation for machine trenching of second side 306.

Figure 15:
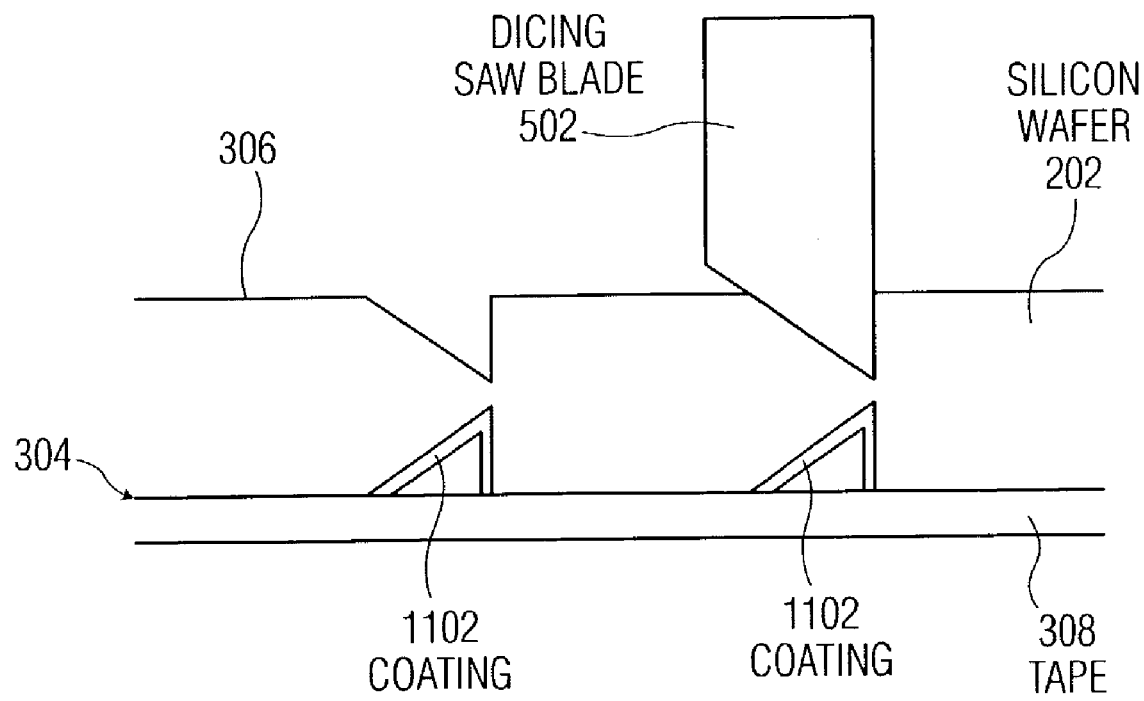
FIG. 15 illustrates a cross-section view of a dicing saw blade machining a second trench in a silicon wafer that is tape mounted according to an embodiment of the present invention.
Figure 16:
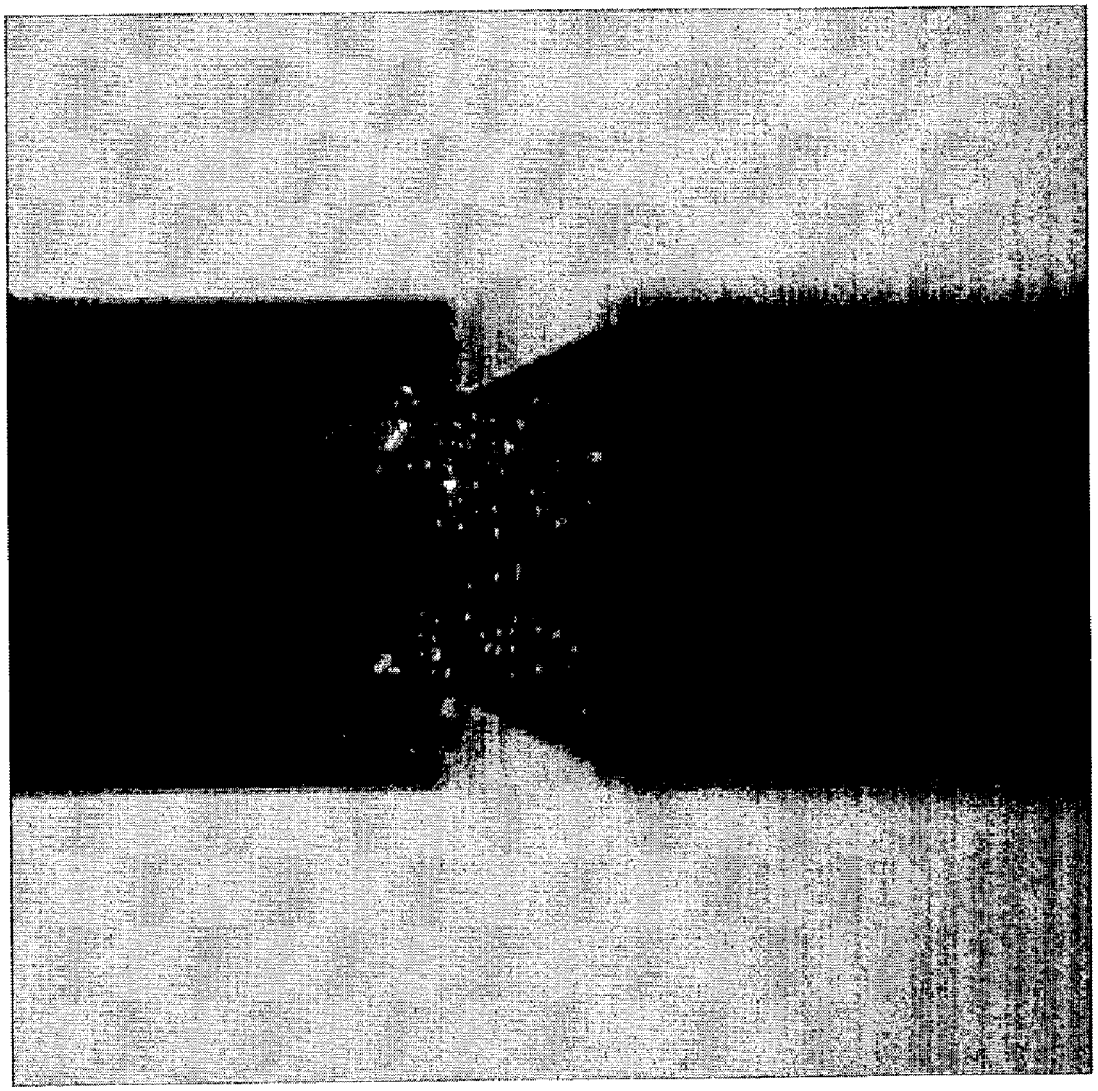
FIG. 16 illustrates a cross-section image of a silicon wafer that has been machined trenched on both sides according to an embodiment of the present invention.

Step 2004 is then performed on silicon wafer 202. In step 2004, trenches are machined into second side 306 of silicon wafer 202, as was done in step 1008, in order to create double bevel silicon based surgical blades. FIG. 15 illustrates a cross-section view of a dicing saw blade 502 machining a second trench in silicon wafer 202 that is tape mounted, according to an embodiment of the invention. Of course, excimer laser 902, ultrasonic machine tool 100 or the hot-forging process can also be used to machine the second trench in silicon wafer 202. In FIG. 15, dicing saw blade 502 is shown machining a second trench onto second side 306 of silicon wafer 202. Coating 1102 is shown having been optionally applied in step 2002. FIGS. 10A and 10B show the resulting single and double bevel cuts respectively. In FIG. 10A a single cut has been made on the silicon wafer 202 resulting in cutting angle Φ in a single blade assembly. In FIG. 10B, a second trench has been machined into silicon wafer 202 (by any of the aforementioned trench machining processes) with the same angle as the first trench. The result is a double bevel silicon based surgical blade, with each cutting edge exhibiting a cutting angle of Φ, yielding a double bevel angle of 2101. FIG. 16 illustrates a cross-section image of a silicon wafer that has been machined trenched on both sides, according to an embodiment of the invention.

Following machine trench step 2004, a decision must be made in decision step 2005, as to whether to etch the double machine trenched silicon wafer 202 in step 1018, or dice the double machine trenched silicon wafer 202 in step 1016. Dicing step 1016 can be performed by a dicing saw blade, laser beam (e.g., an excimer laser, or laser waterjet 402). Dicing provides for the resultant strips to be etched (in step 1018) in custom fixtures in lieu of wafer boats (discussed in detail below).

Figure 17A:
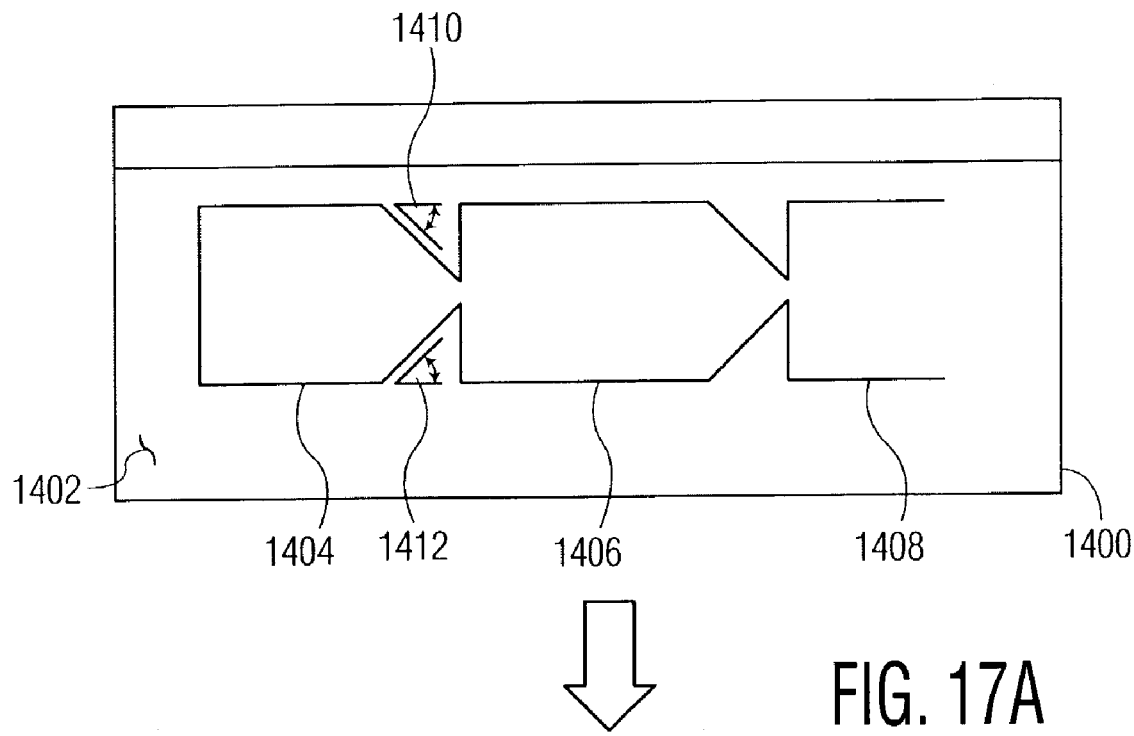
FIGS. 17A and 17B illustrate an isotropic etching process performed on a silicon wafer with machined trenches on both sides according to an embodiment of the present invention.
Figure 17B:
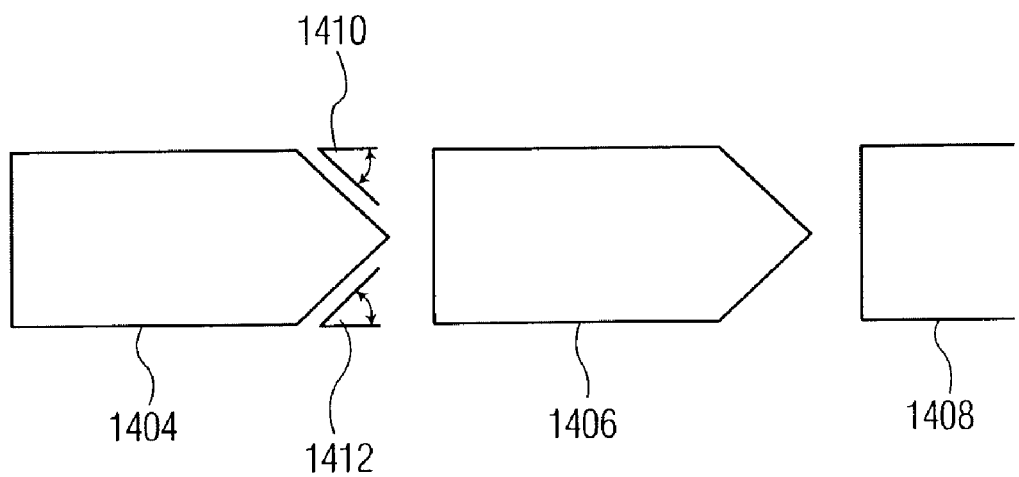

FIGS. 17A and 17B illustrate an isotropic etching process performed on a silicon wafer with machined trenches on both sides, according to an embodiment of the present invention. In etching step 1018, the machined silicon wafer 202 is dismounted from tape 308. Silicon wafer 202 is then placed in a wafer boat and immersed in an isotropic acid bath 1400. The etchant's 1402 temperature, concentration and agitation are controlled to maximize the uniformity of the etch process. The preferred isotropic etchant 1402 used is comprised of hydrofluoric acid, nitric acid, and acetic acid (HNA). Other combinations and concentrations can be used to achieve the same purpose. For example, water can be exchanged for the acetic acid. Spray etching, isotropic xenon diflouride gas etching, and electrolytic etching, in lieu of immersion etching, can also be used to achieve the same results. Another example of a compound that can be used in gas etching is sulfur hexafluoride, or other similar fluorinated gases.

The etching process will uniformly etch both sides of silicon wafer 202 and its respective trenches until the opposing trench profiles intersect. Silicon wafer 202 will be immediately removed from etchant 1402 and rinsed once this occurs. The expected cutting edge radius attained by this process ranges from 5 nm to 500 nm.

Isotropic chemical etching is a process that is used to remove silicon in a uniform manner. In the manufacturing process according to an embodiment of the present invention, the wafer surface profile that was produced with the machining described above is uniformly brought down to intersect with the profile on the opposing side of the wafer (if single bevel blades are desired, the non-machined opposing silicon wafer surface will be intersected). Isotropic etching is used in order to achieve the desired blade sharpness while preserving the blade angle. Attempts to intersect the wafer profiles by machining alone fail because the desired edge geometry is too delicate to withstand the machining mechanical and thermal forces. Each of the acidic components of isotropic etchant (etchant) 1402 has a specific function in isotropic acid bath 1400. First, nitric acid oxidizes the exposed silicon, and secondly, hydrofluoric acid removes the oxidized silicon. Acetic acid acts as a diluent during this process. Precise control of composition, temperature and agitation is necessary to achieve repeatable results.

In FIG. 17A silicon wafer 202, with no coating 1102, has been placed in isotropic etch bath 1400. Note that each surgical blade, first surgical blade 1404, second surgical blade 1406, and third surgical blade 1408, are connected to each other. As etchant 1402 works on the silicon, one layer after another of molecules is removed over time, decreasing the width of the silicon (i.e., the surgical blade) until the two angles, 1410 and 1412 (of first surgical blade 1404), intersect at the point where they are joined to the next surgical blade (second surgical blade 1406). The result is that several surgical blades (1404, 1406 and 1408) are formed. Note that the same angles have been maintained throughout the isotropic etching process, except that less silicon material remains because it has been dissolved by etchant 1402.

Figure 18A:
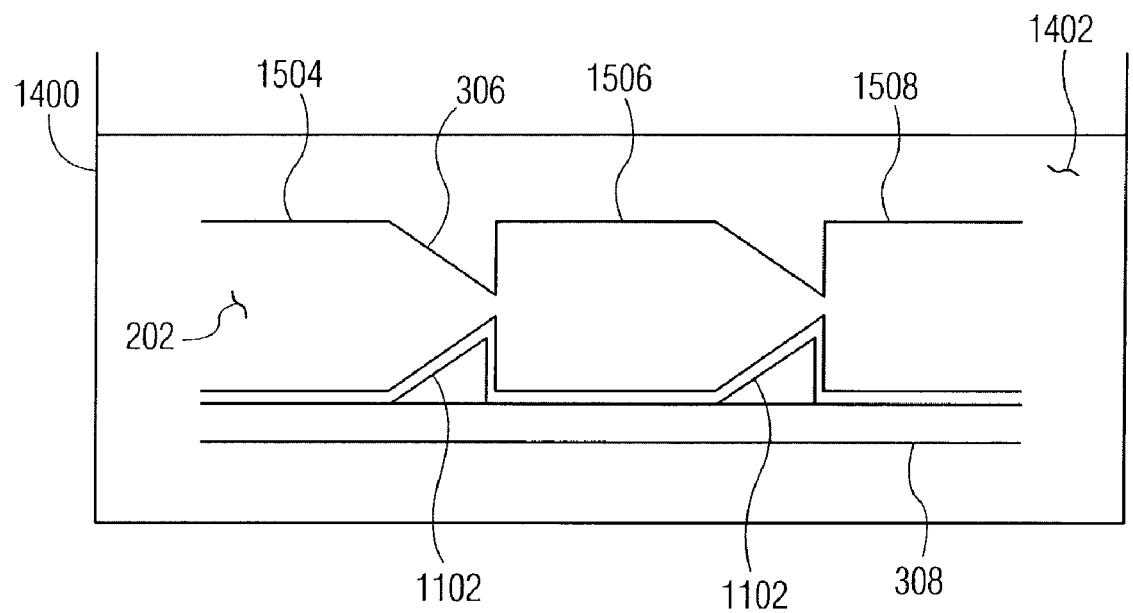
FIGS. 18A and 18B illustrate an isotropic etching process on a silicon wafer with machined trenches on both sides, and a coating layer on one side according to an embodiment of the present invention.
Figure 18B:
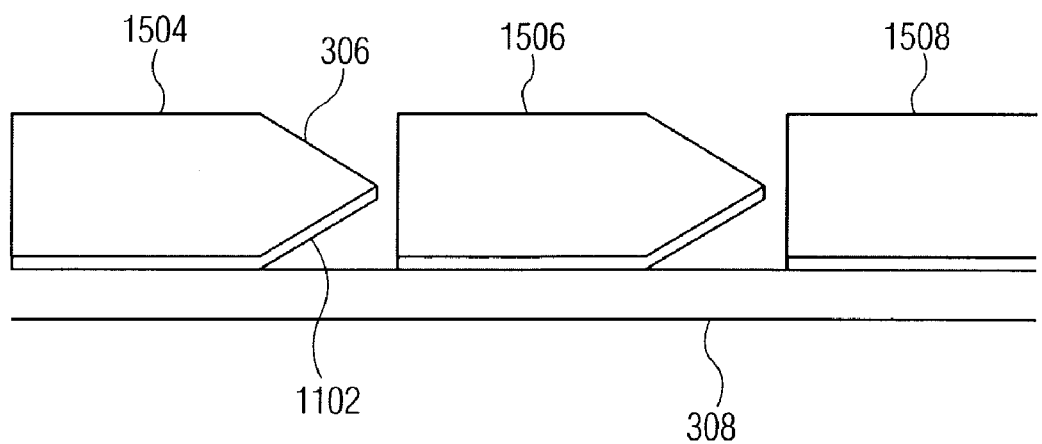

FIGS. 18A and 18B illustrate an isotropic etching process on a silicon wafer with machined trenches on both sides, and a coating layer on one side, according to another embodiment of the present invention. In FIGS. 18A and 18B, tape 308 and coating 1102 have been left on silicon wafer 202 so that the etching process only acts upon second side 306 of silicon wafer 202. It is not necessary that the wafer be mounted on tape during the etching process; this is only a manufacturing option. Again, isotropic etch material 1402 works upon the exposed silicon wafer 202 solely, removing silicon material (one layer after another), but maintaining the same angle as was machined in step 2004 (because this is second side 306). As a result, in FIG. 18B, silicon based surgical blades 1504, 1506 and 1508 have the same angle as was machined in steps 1008 and 2004, on first side 304, because of tape 308 and optional coating 1102, and on second side 306, because isotropic etchant 1402 removes uniform layers of silicon molecules along the machined trench surface. First side 304 of silicon wafer 202 has not been etched at all, providing additional strength to the finished silicon based surgical blade.

Another benefit of using optional step 2002, applying coating 1102 to first side 304 of silicon wafer 202, is that the cutting edge (the first machined trench side) is composed of coating 1102 (which is preferably comprised of a layer of silicon nitride) that possesses stronger material properties than the base silicon material. Therefore, the process of applying coating 1102 results in a cutting edge that is stronger and more durable. Coating 1102 also provides a wear-barrier to the blade surface which can be desirable for blades that come in contact with steel in electromechanical reciprocating blade devices. Table I illustrates typical strength-indicating specifications of a silicon based surgical blade manufactured without coating 1102 (silicon) and with coating 1102 (silicon nitride).

TABLE I

| Property | Silicon | Silicon Nitride |
|---|---|---|
| Young's Modulus (GPa) | 160 | 323 |
| Yield Strength (GPa) | 7 | 14 |

Young's Modulus (also known as the modulus of elasticity) is a measurement of a material's inherent stiffness. The higher the modulus, the stiffer the material. Yield strength is the point at which a material, under load, will transition from elastic to plastic deformation. In other words, it is the point at which the material will no longer flex, but will permanently warp or break. After etching (with or without coating 1102), the etched silicon wafer 202 is thoroughly rinsed and cleaned to remove all residual etchant 1402 chemicals.

Figure 19:
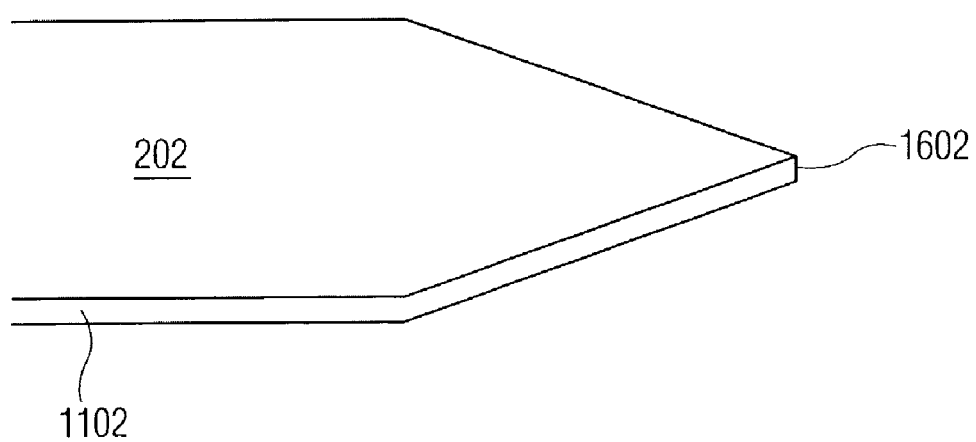
FIG. 19 illustrates a resultant cutting edge of a double bevel silicon surgical blade with a coating on one side manufactured according to an embodiment of the present invention.

FIG. 19 illustrates a resultant cutting edge of a double bevel silicon surgical blade with a coating on one side manufactured according to an embodiment of the present invention. The cutting edge 1602 typically has a radius of 5 to 500 nanometers which is similar to that of a diamond surgical blade, but manufactured at much less cost. After the etching process of step 1018 has been performed, silicon based surgical blades can be mounted according to step 1020, which is the same as mounting steps 1002 and step 2003.

Following mounting step 1020, the silicon based surgical blades (silicon blades) can be singulated in step 1022, which means that each silicon blade is cut apart through use of a dicing saw blade, laser beam (e.g., laser waterjet 402 or an excimer laser), or other suitable means to separate the silicon blades from each other. As one skilled in the art can appreciate, lasers with certain wavelengths within the range of 150 nm to 11,000 nm can also be used. An example of a laser in this wavelength range is an excimer laser. The uniqueness of the laser waterjet (a YAG laser) is that it can scroll curvilinear, interrupted patterns in the wafer. This provides the manufacturer the flexibility to make virtually an unlimited number of non-cutting edge blade profiles. The laser waterjet uses a stream of water as a waveguide that allows the laser to cut like a band saw. This cannot be achieved with the current state of the art dicing machines, which, as mentioned above, can only dice in continuous, straight-line patterns.

In step 1024 the singulated surgical silicon blades are picked and placed on blade handle assemblies, according to the particular desires of the customers. Prior to actual "picking and placing" however, the etched silicon wafers 202 (being mounted on either tape and frame or on a tape/wafer frame) are radiated by ultraviolet (UV) light in the wafer mounting machine to reduce tape 308 tackiness. Silicon wafers 202, still on the "reduced tackiness" tape and frame, or tape/wafer frame, are then loaded into a commercially available die-attach assembly system. Recall from above it was discussed that the order of certain steps can be interchanged according to various manufacturing environments. One such example are the steps of singulation and radiation by UV light: these steps can be interchanged if necessary.

The die-attach assembly system will remove the individual etched silicon surgical blades from the "reduced tackiness" tape and wafer or tape/wafer frame, and will attach the silicon surgical blades to their respective holders within the desired tolerance. An epoxy or adhesive will be used to mount the two components. Other assembly methods can be used to attach the silicon surgical blade to its respective substrate, including heat staking, ultrasonic staking, ultrasonic welding, laser welding or eutectic bonding. Lastly in step 1026, the fully assembled silicon surgical blades with handles, are packaged to ensure sterility and safety, and transported for use according to the design of the silicon surgical blade.

Figure 24:
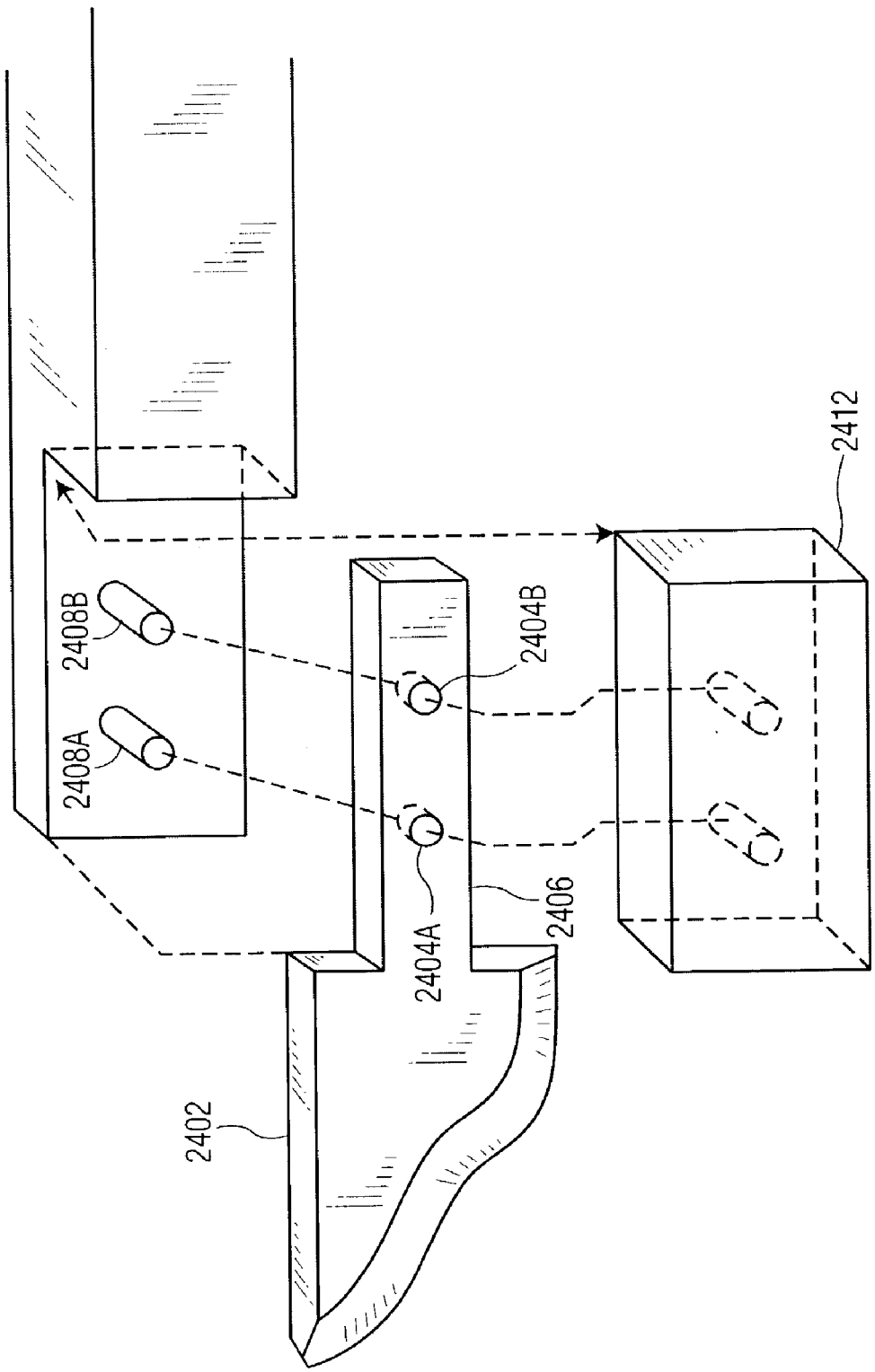
FIG. 24 illustrates a post-slot assembly of a handle and a surgical blade manufactured in accordance with an embodiment of the invention.

Another assembly method that can be used to mount the surgical blade to its holder involves another use of slots. Slots, as discussed above, can be created by the laser water-jet or excimer laser, and were used to provide an opening for the dicing saw blade to engage the silicon wafer 202 when machining trenches. An additional use of slots can be to provide a receptacle in the blade for one or more posts in a holder. FIG. 24 illustrates such an arrangement. In FIG. 24, finished surgical blade 2402 has had two slots 2404a, 2404b created in its holder interface region 2406. These interface with posts 2408a, 2408b of blade holder 2410. The slots can be cut into the silicon wafer 202 at any point in the manufacturing process, but preferably can be done prior to singulation of the surgical blades. Prior to being interfaced, an adhesive can be applied to the appropriate areas, assuring a tight hold. Then, cover 2412 can be glued as shown, to provide a finished appearance to the final product. The purpose for implementing the post-slot assembly is that it provides additional resistance to any pulling force that blade 2402 might encounter during a cutting procedure.

Having described the manufacturing process for a double bevel silicon-based surgical blade, attention is turned to FIG. 2, which illustrates a flow diagram of a method for manufacturing a single bevel surgical blade from silicon according to a second embodiment of the present invention. Steps 1002, 1004, 1006, 1008 of FIG. 1 are the same for the method illustrated in FIG. 2, and therefore will not be repeated. However, the method for manufacturing a single bevel surgical blade differs in the next step, step 1010, from the method for manufacturing a double bevel blade, and therefore, will be discussed in detail.

Following step 1008 decision step 1010 determines whether the machined silicon wafer 202 will be dismounted from silicon wafer mounting assembly 204. If the single trench silicon wafers 202 were to be dismounted (in step 1012), then a further option is to dice the single trench wafers in step 1016. In optional dismounting step 1012, the silicon wafer 202 is dismounted from tape 308 utilizing the same standard mounting machine.

If silicon wafer 202 was dismounted in step 1012, then optionally the silicon wafer 202 can be diced (i.e., silicon wafer 202 cut apart into strips) in step 1016. Dicing step 1016 can be performed by a dicing blade, excimer laser 902, or laser waterjet 402. Dicing provides for the resultant strips to be etched (in step 1018) in custom fixtures in lieu of wafer boats (discussed in detail below). Following either the dicing step of 1016, the dismounting step of 1012, or the machine trench step of 1008, the next step in the method for manufacturing a single bevel silicon based surgical blade is step 1018. Step 1018 is the etching step, which has already been discussed in detail above. Thereafter, steps 1020, 1022, 1024 and 1026 follow, all of which have been described in detail above in reference to the manufacture of a double bevel silicon based surgical blade, and therefore do not need to be discussed again.

FIG. 3 illustrates a flow diagram of an alternative method for manufacturing a single bevel surgical blade from silicon according to a third embodiment of the present invention. The method illustrated in FIG. 3 is identical to that illustrated in FIG. 2, through steps 1002, 1004, 1006, 1008. After step 1008 in FIG. 3, however, there is coating step 2002. The coating step 2002 was described above in reference to FIG. 1, and need not be discussed in detail again. The result of the coating step is the same as was described previously: the machined side of silicon wafer 202 has a layer 1102 over it.

Figures 23A, 23B:
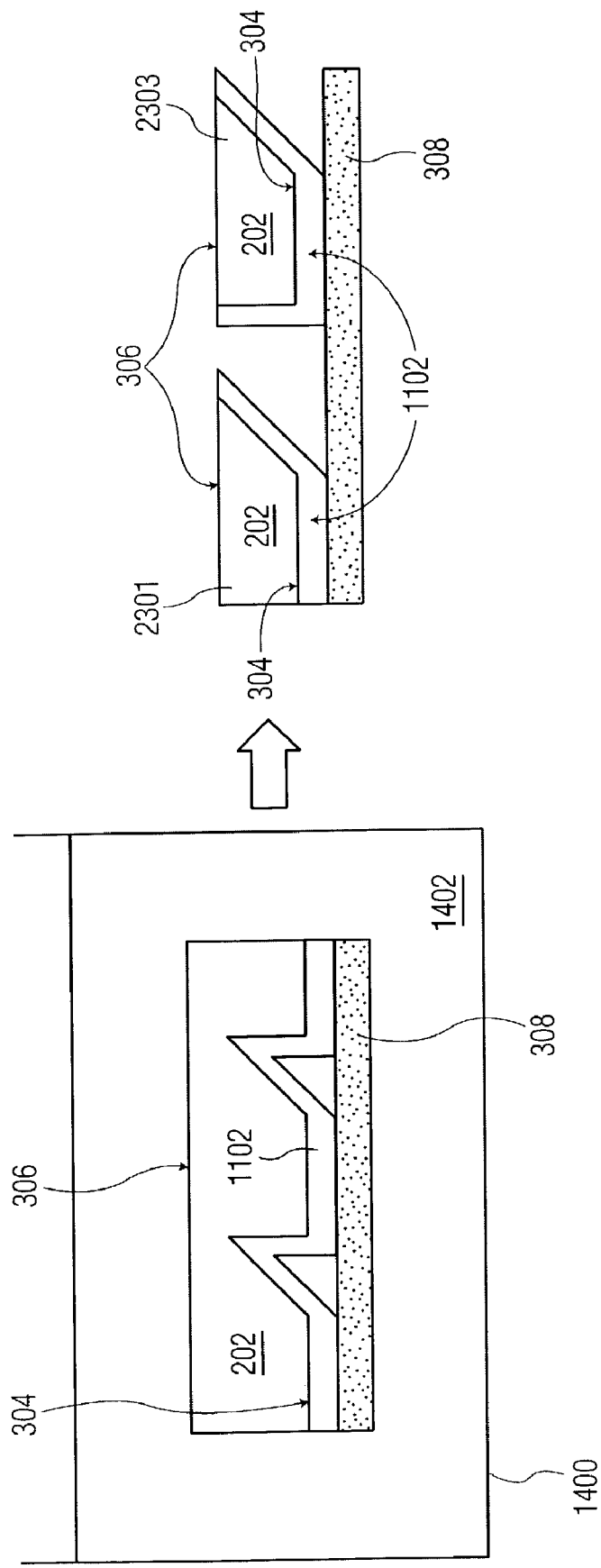
FIGS. 23A and 23B illustrate an isotropic etching process on a silicon wafer with a machined trench on one side, and a coating layer on an opposite side according to a further embodiment of the present invention.

Following the coating step 2002, the silicon wafer 202 is dismounted and remounted in step 2003. This step is also identical as was previously discussed in reference to FIG. 1 (step 2003). The result is that the coated side of silicon wafer 202 is face down on the mounting assembly 204. Thereafter, steps 1018, 1020, 1022, 1024 and 1026 take place, all of which have been described in detail above. The net result is a single bevel surgical blade, with the first side 304 (machined side) provided with a layer of coating 1102 to improve the strength and durability of the surgical blade. FIGS. 23A and 23B illustrate and describe the single bevel coated surgical blade in greater detail.

FIGS. 23A and 23B illustrate an isotropic etching process on a silicon wafer with a machined trench on one side, and a coating layer on an opposite side according to a further embodiment of the present invention. As described above, silicon wafer 202 has coating 1102 applied to first side 304 which is then mounted onto tape 308, thus coming in close contact with it, as shown in FIG. 23A. Silicon wafer 202 is then placed in bath 1400, which contains etchant 1402, as discussed in detail above. Etchant 1402 begins to etch the second side 306 ("top side") of silicon wafer 202, removing one layer after another of silicon molecules. After a period of time, silicon wafer 202 has its thickness reduced by etchant 1402 until second side 306 comes in contact with first side 304 and coating 1102. The result is a silicon nitride coated single bevel silicon based surgical blade. All of the aforementioned advantages of having a silicon nitride (or coated) blade edge apply equally to this type of blade as shown and discussed in reference to FIGS. 18A, 18B and 19.

Figure 20A:
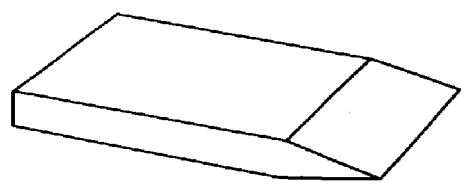
FIGS. 20A–20G illustrate various examples of surgical blades that can be manufactured in accordance with the method of the present invention.
Figure 20B:
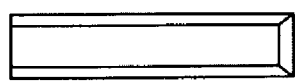
Figure 20C:
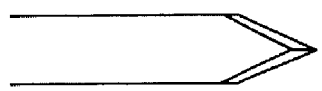
Figure 20D:
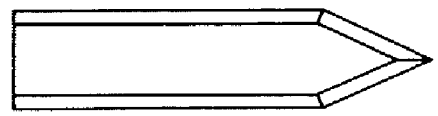
Figure 20E:
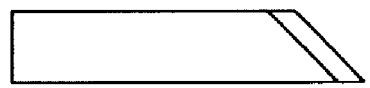
Figure 20F:
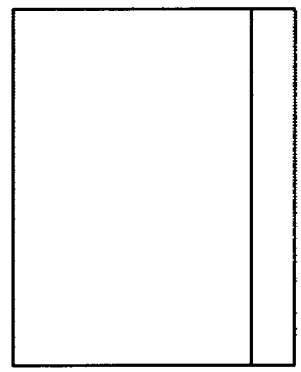
Figure 20G:
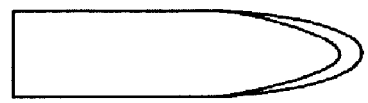

FIGS. 20A–20G illustrate various examples of silicon based surgical blades that can be manufactured in accordance with the method of the present invention. Various blade designs can be manufactured utilizing this process. Blades with single bevels, symmetric and asymmetric double bevels, and curvilinear cutting edges can be produced. For single bevels, the machining is only performed on one side of the wafer. Various blade profiles can be made, such as single edge chisel (FIG. 20A), three edge chisel (FIG. 20B), slit, two edges sharp (FIG. 20C), slit, four edges sharp (FIG. 20D), stab, one edge sharp (FIG. 20E), keratome, one edge sharp (FIG. 20F) and crescent, curvilinear sharp edge (FIG. 20G). The profile angles, widths, lengths, thicknesses, and bevel angles can be varied with this process. This process can be combined with traditional photolithography to produce more variations and features.

Figure 21A:
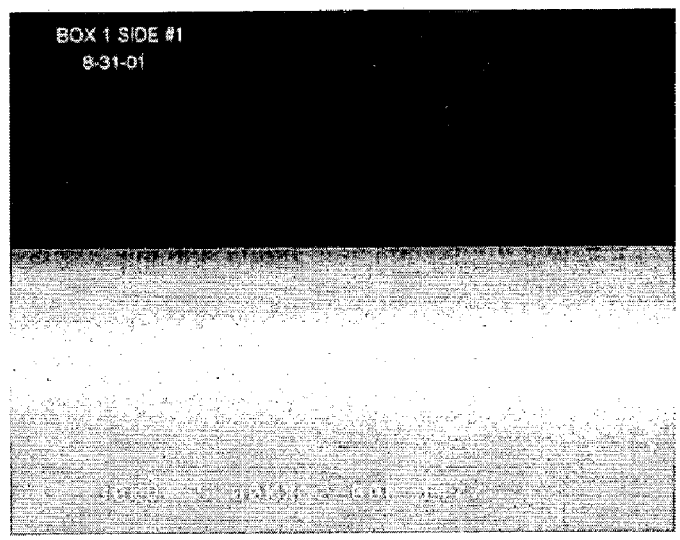
FIGS. 21A and 21B illustrate a side view of the blade edge of a silicon surgical blade manufactured in accordance with an embodiment of the present invention, and a stainless steel surgical blade, at 5,000× magnification, respectively.
Figure 21B:
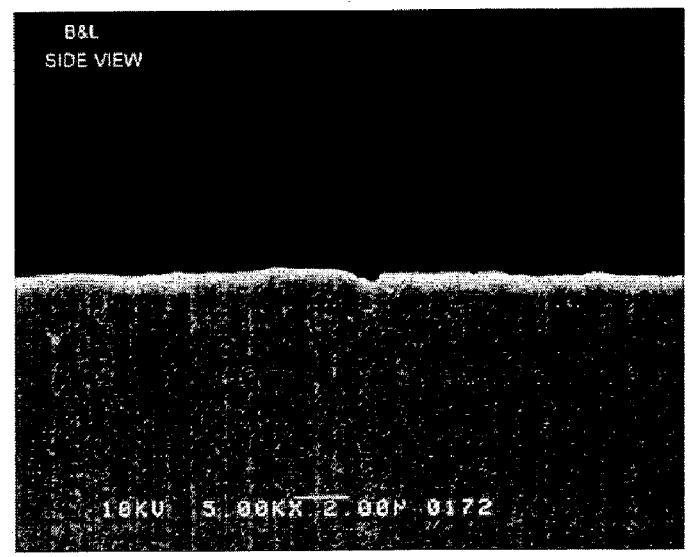
Figure 22A:
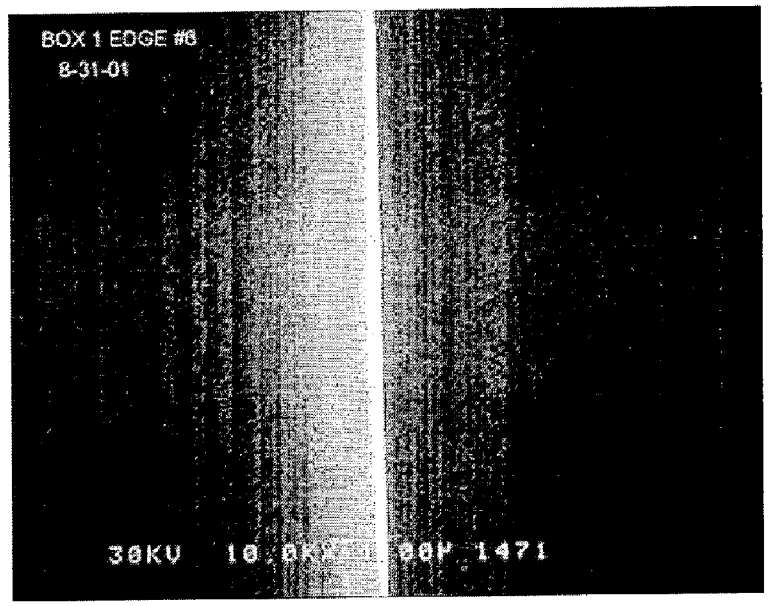
FIGS. 22A and 22B illustrate a top view of the blade edge of a silicon surgical blade manufactured in accordance with an embodiment of the present invention, and a stainless steel blade, at 10,000× magnification, respectively.
Figure 22B:
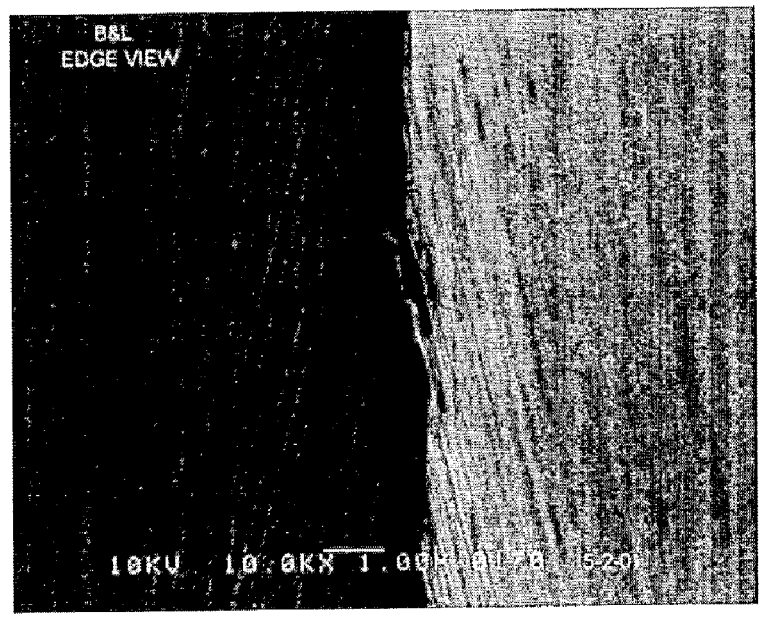

FIGS. 21A and 21B illustrate a side view of a silicon surgical blade manufactured in accordance with an embodiment of the invention, and a stainless steel surgical blade, at 5,000× magnification, respectively. Note the difference between FIGS. 21A and 21B. FIG. 21A is much smoother and more uniform. FIGS. 22A and 22B illustrate top views of the blade edge of a silicon surgical blade manufactured in accordance with an embodiment of the invention and a stainless steel blade, at 10,000× magnification, respectively. Again, the difference between FIG. 22A and FIG. 22B is that the former, the result of the method according to an embodiment of the invention, is much smoother and more uniform than the stainless steel blade of FIG. 22B.

Figure 25A:
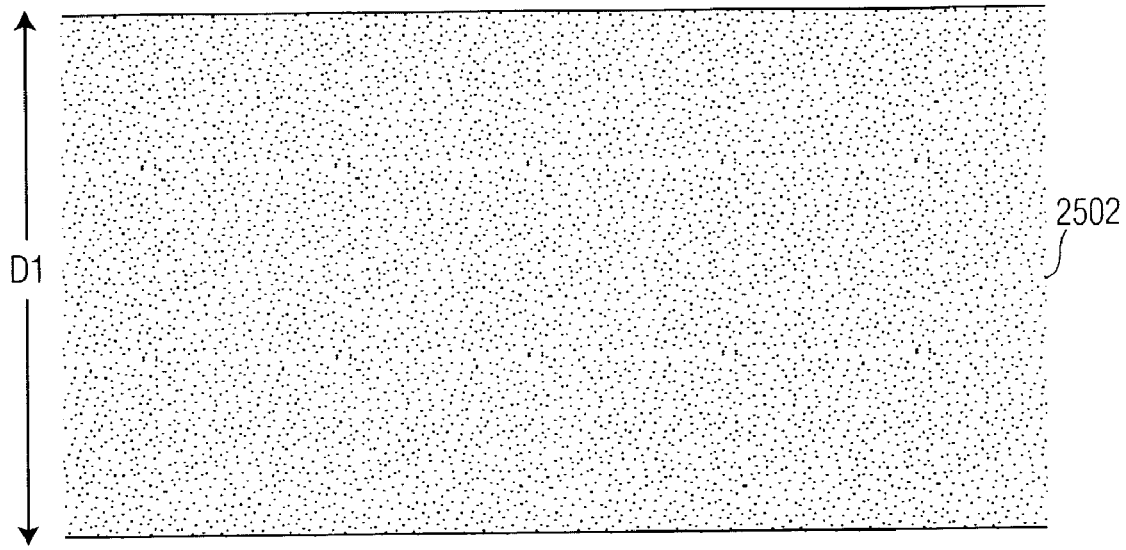
FIGS. 25A and 25B illustrate profile perspectives of a blade edge made of a crystalline material, and a blade edge made of a crystalline material that includes a layer conversion process in accordance with an embodiment of the invention.
Figure 25B:
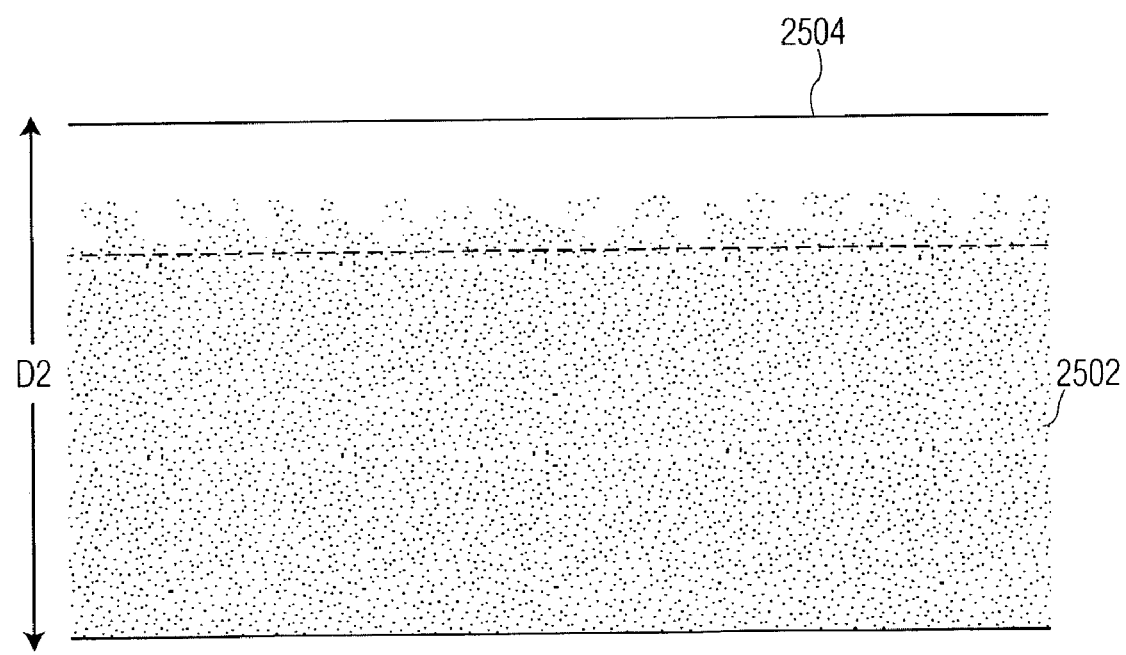

FIGS. 25A and 25B illustrate profile perspectives of a blade edge made of a crystalline material, and a blade edge made of a crystalline material that includes a layer conversion process in accordance with an embodiment of the invention. In another embodiment of the invention, it is possible to chemically convert the surface of the substrate material to a new material 2504 after etching the silicon wafer. This step can also be known as a "thermal oxidation, nitride conversion" or "silicon carbide conversion of the silicon surface" step. Other compounds can be created depending on which elements are allowed to interact with the substrate/blade material. The benefit of converting the surface of the blade to a compound of the substrate material is that the new material/surface can be selected such that a harder cutting edge is created. But unlike a coating, the cutting edge of the blade maintains the geometry and sharpness of the post etch step. Note that in FIGS. 25A and 25B, the depth of the silicon blade has not changed because of the conversion process; "D1" (the depth of the silicon-only blade) is equal to "D2" (the depth of the silicon blade with a conversion layer 2504).

Referring to FIG. 1, after step 1018 a decision is made to convert the surface (decision step 1019). If a conversion layer is to be added ("Yes" path from decision step 1019), a conversion layer is added in step 1021. The method then proceeds to step 1020. If no conversion layer is to be added ("No" path from decision step 1019), the method proceeds to step 1020. The conversion process requires diffusion or high temperature furnaces. The substrate is heated under vacuum or in an inert environment to a temperature in excess of 500° C. Selected gasses are metered into the furnace in controlled concentrations and as a result of the high temperature they diffuse into the silicon. As they diffuse into the silicon they react with the silicon to form a new compound. Since the new material is created by diffusion and chemical reaction with the substrate rather then applying a coating, the original geometry (sharpness) of the silicon blade is preserved. An additional benefit of the conversion process is that the optical index of refraction of the converted layer is different than that of the substrate so the blade appears to be colored. The color depends both on the composition of the converted material and it's thickness.

A single crystal substrate material that has been converted at the surface also exhibits superior fracture and wear resistance than a non converted blade. By changing the surface to a harder material the tendency of the substrate to form crack initiation sites and cleave along crystalline planes is reduced.

A further example of a manufacturing step that can be performed with some interchangeability is the matte-finish step. Often, especially when manufactured in the preferred embodiment of surgical blades, the silicon surface of the blade will be highly reflective. This can be distracting to the surgeon if the blade is being used under a microscope with a source of illumination. Therefore, the surface of the blade can be provided with a matte finish that diffuses incident light (from a high-intensity lamp used during surgical procedure, for example), making it appear dull, as opposed to shiny. The matte finish is created by radiating the blade surface with a suitable laser, to ablate regions in the blade surface according to specific patterns and densities. The ablated regions are made in the shape of a circle because that is generally the shape of the emitted laser beam, though that need not be the case. The dimension of the circular ablated regions ranges from 25–50 microns in diameter, and again is dependent upon the manufacturer and type of laser used. The depth of the circular ablated regions ranges from 10–25 microns.

The "density" of circular ablated regions refers to the total percentage surface area covered by the circular ablated regions. An "ablated region density" of about 5% dulls the blade noticeably, from its normally smooth, mirror-like appearance. However, co-locating all the ablated regions does not affect the mirror-like effect of the balance of the blade. Therefore, the circular ablated regions are applied throughput the surface area of the blade, but in a random fashion. In practice, a graphic file can be generated that randomly locates the depressions, but achieves the desired effect of a specific ablated region density and randomness to the pattern. This graphic file can be created manually, or automatically by a program in a computer. An additional feature that can be implemented is the inscription of serial numbers, manufacturer logos, or the surgeon's or hospital's name on the blade itself.

Typically, a gantry laser can be used to create the matte finish on the blades, or a galvo-head laser machine. The former is slow, but extremely accurate, and the latter is fast, but not as accurate as the gantry. Since the overall accuracy is not vital, and speed of manufacturing directly affects cost, the galvo-head laser machine is the preferred tool. It is capable of moving thousands of millimeters per second, providing an overall ablated region etch time of about five seconds for a typical surgical blade.

The present invention has been described with reference to certain exemplary embodiments thereof. However, it will be readily apparent to those skilled in the art that it is possible to embody the invention in specific forms other than those of the exemplary embodiments described above. This may be done without departing from the spirit and scope of the invention. The exemplary embodiment is merely illustrative and should not be considered restrictive in any way. The scope of the invention is defined by the appended claims and their equivalents, rather than by the preceding description.

What is claimed is:

1. A method for manufacturing a cutting device from a crystalline material, the method comprising:
    machining at least one blade profile in a wafer of crystalline material on a first side of the wafer of the crystalline material;
    isotropically etching the wafer of crystalline material to form at least one surgical blade comprising the at least one blade profile; and
    singulating the at least one surgical blades.

2. The method according to claim 1, wherein the machining step comprises:
    machining at least one blade profile in the wafer of crystalline material with a dicing saw blade.

3. The method according to claim 1, wherein the machining step comprises:
    machining at least one blade profile in the wafer of crystalline material with a laser beam.

4. The method according to claim 3, wherein the laser beam is produced by an excimer laser or a laser waterjet.

5. The method according to claim 1, wherein the machining step comprises:
    machining at least one blade profile in the wafer of crystalline material with an ultrasonic machine.

6. The method according to claim 1, wherein the machining step comprises:
    machining at least one blade profile in the wafer of crystalline material with a hot forging process.

7. The method according to claim 1, wherein the etching step comprises:
    placing the wafer of crystalline material with at least one blade profile on a wafer boat;
    immersing the wafer boat and wafer of crystalline material with at least one blade profile in an isotropic acid bath;
    etching the crystalline material in a uniform manner such that the crystalline material is removed in a uniform manner on any exposed surface, whereby a sharp surgical blade edge is etched in the shape of the at least one blade profile.

8. The method according to claim 7, wherein the isotropic acid bath comprises:
    a mixture of hydrofluoric acid, nitric acid and acetic acid.

9. The method according to claim 7, wherein the isotropic acid bath comprises:
    a mixture of hydrofluoric acid, nitric acid and water.

10. The method according to claim 1, wherein the etching step comprises:
    placing the wafer of crystalline material with at least one blade profile in a wafer boat;
    spraying a spray etchant at the wafer boat and wafer of crystalline material with at least one blade profile;
    etching the crystalline material in a uniform manner with the spray etchant such that the crystalline material is removed in a uniform manner on any exposed surface, whereby a sharp surgical blade edge is etched in the shape of the at least one blade profile.

11. The method according to claim 1, wherein the etching step comprises:
    placing the wafer of crystalline material with at least one blade profile on a wafer boat;
    immersing the wafer boat and wafer of crystalline material with at least one blade profile in an isotropic xenon difluoride, sulfur hexafluoride or similar fluorinated gas environment;
    etching the crystalline material in a uniform manner with the isotropic xenon difluoride, sulfur hexafluoride or similar fluorinated gas such that the crystalline material is removed in a uniform manner on any exposed surface, whereby a sharp surgical blade edge is etched in the shape of the at least one blade profile.

12. The method according to claim 1, wherein the etching step comprises:
    placing the wafer of crystalline material with at least one blade profile in a wafer boat;
    immersing the wafer boat and wafer of crystalline material with at least one blade profile in an electrolytic bath;
    etching the crystalline material in a uniform manner with the electrolytic bath such that the crystalline material is removed in a uniform manner on any exposed surface, whereby a sharp surgical blade edge is etched in the shape of the at least one blade profile.

13. The method according to claim 1, wherein the singulating step comprises:
    dicing the machined wafer of crystalline material with a dicing blade.

14. The method according to claim 1, wherein the singulating step comprises:
    dicing the machined wafer of crystalline material with a laser beam.

15. The method according to claim 1, wherein the laser beam is produced by an excimer laser or a laser waterjet.

16. The method according to claim 1, further comprising:
    dicing the machined wafer of crystalline material profiles after machining the at least one blade profile in the form of single bevel surgical blade and prior to the step of etching.

17. The method according to claim 16, wherein the dicing step comprises:
    dicing the machined wafer of crystalline material with a dicing blade.

18. The method according to claim 16, wherein the dicing step comprises:
    dicing the machined wafer of crystalline material with a laser beam.

19. The method according to claim 18, wherein the laser beam is produced by an excimer laser or a laser waterjet.

20. The method for manufacturing a surgical blade from a crystalline material according to claim 1, further comprising:
    machining at least one second blade profile in the wafer of crystalline material on a second side of the wafer of crystalline material prior to the step of etching.

21. The method according to claim 20, further comprising:
coating the first side of the machined wafer of crystalline material.

22. The method according to claim 21, wherein the coating step comprises:
coating the first side of the machined wafer of crystalline material with a layer of material selected from the group consisting of silicon nitride, titanium nitride, aluminum titanium nitride, silicon dioxide, silicon carbide, titanium carbide, boron nitride, and diamond-like-crystals.

23. The method according to claim 20, further comprising:
dicing the machined wafer of crystalline material into separated machined double beveled blade profiles after machining the at least one second blade profile in the second side and prior to the step of etching.

24. The method according to claim 23, wherein the dicing step comprises:
dicing the machined wafer of crystalline material with a dicing blade.

25. The method according to claim 23, wherein the dicing step comprises:
dicing the machined wafer of crystalline material with a laser beam.

26. The method according to claim 25, wherein the laser beam is produced by an excimer laser or a laser waterjet.

27. The method according to claim 1, further comprising:
coating the first side of the wafer of crystalline material after the step of machining the wafer of crystalline material; and
mounting the wafer of crystalline material on its first side prior to the step of etching.

28. The method according to claim 27, wherein the coating step comprises:
coating the first side of the formed wafer of crystalline material with a layer of material selected from the group consisting of silicon nitride, titanium nitride, aluminum titanium nitride, silicon dioxide, silicon carbide, titanium carbide, boron nitride, and diamond-like-crystals.

29. The method according to claim 1, wherein the crystalline material comprises silicon.

30. A method for manufacturing a cutting device from a crystalline material, comprising:
mounting a wafer of crystalline material on a mounting assembly;
pre-cutting the mounted wafer of crystalline material, such that a plurality of through hole fiducials are cut to assist in the machining step;
machining at least one blade profile in the wafer of crystalline material on its first side;
etching the wafer of crystalline material to form at least one surgical blade;
singulating the etched crystalline material surgical blades; and
radiating the singulated etched crystalline material surgical blades with ultra-violet light, to separate them from the mounting assembly, in preparation for packaging for sale.

31. The method according to claim 30 wherein the pre-cutting step comprises:
pre-cutting through hole fiducials in the mounted wafer of crystalline material with a laser beam.

32. The method according to claim 31 wherein the laser beam is produced by an excimer laser or a laser waterjet.

33. The method according to claim 30 wherein the pre-cutting step comprises:
pre-cutting through hole fiducials in the mounted wafer of crystalline material using a mechanical machining device.

34. The method according to claim 33 wherein the mechanical machining device comprises a drilling tool, ultrasonic machining tool or a mechanical grinding device.

35. The method according to claim 30 wherein the crystalline material comprises silicon.

36. A method for manufacturing a cutting device from a crystalline material, comprising:
mounting a wafer of crystalline material on a mounting assembly;
pre-cutting the mounted wafer of crystalline material, such that a plurality slots are cut to assist in the machining step;
machining at least one blade profile in the wafer of crystalline material on its first side;
etching the wafer of crystalline material to form at least one surgical blade;
singulating the etched crystalline material surgical blades; and
radiating the singulated etched crystalline material surgical blades with ultra-violet light, to separate them from the mounting assembly, in preparation for packaging for sale.

37. The method according to claim 36 further comprising:
pre-cutting slots in the mounted wafer of crystalline material with a laser beam a distance away from the edge of the crystalline material; and
machining the at least one blade profile with a dicing saw blade that engages the crystalline wafer at the pre-cut slot.

38. The method according to claim 37, wherein the laser beam is produced by an excimer laser or a laser waterjet.

39. The method according to claim 36 further comprising:
pre-cutting slots in the mounted wafer of crystalline material with a mechanical machining device a distance away from the edge of the crystalline material; and
machining the at least one blade profile with a dicing saw blade that engages crystalline wafer at the pre-cut slot.

40. The method according to claim 39, wherein the mechanical machining device comprises a drilling tool, ultrasonic machining tool or a mechanical grinding device.

41. The method according to claim 36 wherein the crystalline material comprises silicon.

42. A method for manufacturing a cutting device, the method comprising:
pre-cutting a wafer of a crystalline material, such that a plurality of through hole fiducials are cut to assist in a machining step;
machining at least one blade profile in the wafer of the crystalline material; and
etching the wafer of crystalline material to form at least one surgical blade.

43. The method according to claim 42, further comprising singulating the at least one surgical blade.

44. The method according to claim 42, wherein the etching of the wafer comprises isotropically etching the wafer of the crystalline material to form the at least one surgical blade comprising the at least one blade profile.

45. The method according to claim 44 further comprising:
mounting the wafer of the crystalline material on a mounting assembly; and radiating the singulated surgical blade with ultra-violet light, to separate the singulated surgical blade from the mounting assembly.

46. A method for manufacturing a cutting device, the method comprising:

pre-cutting a wafer of a crystalline material, such that a plurality of slots are cut to assist in a machining step;

machining at least one blade profile in the wafer of the crystalline material; and etching the wafer of crystalline material to form at least one surgical blade.

47. The method according to claim 46, further comprising singulating the at least one surgical blade.

48. The method according to claim 46, wherein the etching of the wafer comprises isotropically etching the wafer of the crystalline material to form the at least one surgical blade comprising the at least one blade profile.

49. The method according to claim 48 further comprising:

mounting the wafer of the crystalline material on a mounting assembly; and radiating the singulated surgical blade with ultra-violet light, to separate the singulated surgical blade from the mounting assembly.

* * * * *